(12) United States Patent
Hake et al.

(10) Patent No.: US 8,097,768 B2
(45) Date of Patent: Jan. 17, 2012

(54) METHOD OF ENHANCING QUALITY FACTORS IN COTTON

(75) Inventors: Kater Davis Hake, Germantown, TN (US); Kent Dean Chapman, Denton, TX (US); Thomas Arthur Kerby, Scott, MS (US); Thomas Rainey Speed, Wolfforth, TX (US)

(73) Assignee: University of North Texas, Denton, TX (US)

( * ) Notice: Subject to any disclaimer, the term of this patent is extended or adjusted under 35 U.S.C. 154(b) by 0 days.

(21) Appl. No.: 11/449,873

(22) Filed: Jun. 9, 2006

(65) Prior Publication Data

US 2007/0028330 A1     Feb. 1, 2007

Related U.S. Application Data

(60) Provisional application No. 60/688,706, filed on Jun. 9, 2005, provisional application No. 60/781,744, filed on Mar. 14, 2006.

(51) Int. Cl.
*A01H 5/00* (2006.01)
*C12N 15/82* (2006.01)

(52) U.S. Cl. ......... 800/278; 800/298; 800/281; 435/419

(58) Field of Classification Search ........................ None
See application file for complete search history.

(56) References Cited

U.S. PATENT DOCUMENTS

| | | | |
|---|---|---|---|
| 5,917,127 A | 6/1999 | Willmitzer et al. | |
| 5,981,852 A | 11/1999 | Van Assche et al. | |
| 6,372,965 B1 * | 4/2002 | Lightner et al. | 800/281 |
| 6,444,876 B1 | 9/2002 | Lassner et al. | |
| 2004/0133944 A1 | 7/2004 | Hake et al. | |
| 2004/0221335 A1 * | 11/2004 | Shewmaker et al. | 800/281 |

FOREIGN PATENT DOCUMENTS

WO    WO 2004/063333 A2    7/2004

OTHER PUBLICATIONS

Chapman (2001) JAOCS 78:941-947.*
May, (14th EFS System Conference, 1-13, 2001, Greenville, SC).*
Jepson et al. Chemical-Inducible Gene Expression Systems for Plants.a Review Pestic. Sci. 1998, 54, 360-367.*
Haigler Candace H et al: "Biotechnological improvement of cotton fibre maturity" *Physiologia Plantarum*, vol. 124, No. 3, Jul. 2005, pp. 285-294, XP009076684 ISSN: 0031-9317.

Sunilkumar Ganesan et al: "A comprehensive study of the use of a homologous promoter in antisense cotton lines exhibiting a high seed oleic acid phenotype," *Plant Biotechnology Journal* (Print) May 2005, vol. 3, No. 3, May 2005, pp. 319-330, XP009076682, ISSN: 1467-7652.
Auld et al., "Chemical mutagenesis as a tool in cotton improvement," *Proceedings of the Beltwide Cotton Conf.*, 1, pp. 550-552, 1998.
Chapman et al., "Transgenic cotton plants with increased seed oleic acid content," *J. Am. Oil Chemists Soc.*, 78(9), pp. 941-947, 2001.
Dani, R.G., "Genetic improvement of seed oil content, following indirect selection for earliness and fibre yield in cotton (*Gossypium hirsutum* L.)," *Adv. Plant Sci.*, 12, pp. 479-492, 1999.
Dehesh et al., "Overexpression of 3-ketoacyl-acyl-carrier protein synthase IIIs in plants reduces the rate of lipid synthesis," *Plant Physiol.*, 125, pp. 1103-1114, 2001.
Dhadialla et al., "New insecticides with ecdysteroidal and juvenile hormone activity," *Annu. Rev. Entomol.*, 43, pp. 545-569, 1998.
Dudley et al., "Ninety generations of selection for oil and protein in maize," *Maydica*, 37, pp. 81-87, 1992.
Fehr et al., "Backcross Method," In: *Principles of Cultivar Development*, vol. 1, Chapter 28, Walter R. Fehr. pp. 360-376, (1987).
Focks et al., "wrinkled1: A Novel, low-seed-oil mutant of arabidopsis with a deficiency in the seed-specific regulation of carbohydrate metabolism," *Plant Physiol.*, 118, pp. 91-101, 1998.
Hoang et al., "Biochemical and Molecular Inhibition of Plastidial Carbonic Anhydrase Reduces the Incorporation of Acetate into Lipids in Cotton Embryos and Tobacco Cell Suspensions and Leaves," *Plant Physiol.*, 128, pp. 1417-1427, 2002.
Lauterbach et al., "Yield enhancement in cotton," In: Genetic Control of Cotton Fiber and Seed Quality, Cotton Inc., pp. 104-109, 2000.
Liu et al., "High-stearic and high-oleic cottonseed oils produced by hairpin RNA-mediated post-transcriptional gene silencing," *Plant Physiol.*, 129, pp. 1732-1743, 2002.
Lu et al., "*Arabidopsis* Mutants Deficient in Diacylglycerol Acyltransferase Display Increased Sensitivity to Abscisic Acid, Sugars, and Osmotic Stress during Germination and Seedling Development," *Plant Physiol.*, 129, pp. 1352-1358, 2002.
Rohr et al., "Tandem inverted repeat system for selection of effective transgenic RNAi strains," *The Plant Journal*, 40, pp. 611-621, 2004.
Voelker et al., "Variations in the biosynthesis of seed-storage lipids," *Plant Physiol.*, 52, pp. 335-361, 2001.

* cited by examiner

*Primary Examiner* — Elizabeth McElwain
(74) *Attorney, Agent, or Firm* — Jackson Walker L.L.P.

(57) ABSTRACT

Preferred embodiments of this invention relate to a method for increasing fiber yield in a cotton plant by regenerating a whole cotton plant from a plant cell that has been transformed with a dominant negative allele for an endoplasmic reticulum located gene. The expression of this gene results in suppression of oil and protein biosynthesis in the developing seed and increased production of fiber in the plant.

4 Claims, 17 Drawing Sheets

** p<0.00001

** p<0.05 vs null group or Coker 312 control

* $p<0.001$ vs null or control

METHOD OF ENHANCING QUALITY FACTORS IN COTTON

CROSS-REFERENCE TO RELATED APPLICATIONS

This application claims priority to Provisional application Ser. No. 60/688,706, filed Jun. 9, 2005 and to Provisional application Ser. No. 60/781,744, filed Mar. 14, 2006.

BACKGROUND

I. Technical Field

This invention relates generally to the field of agriculture and molecular biological modification of crops. Specifically, this invention relates to a method for enhancing quality factors in plants and particularly in cotton (e.g., *Gossypium hirsutum* L., *G. barbadense* L., *G. arboreum* and *G. herbaceum*). In preferred embodiments, the invention involves generating transgenic cotton plants that contain genetic systems to suppress seed-oil, protein and/or macronutrients, such as nitrogen (N), phosphorous (P) and potassium (K) in cotton seed. These preferred embodiments involve producing transgenic cotton plants that contain within their genomes genetic systems that modulate, suppress or deactivate the storage systems for oil, protein, phytate and/or macronutrients when a plant is grown to produce fiber. Particular preferred embodiments provide a method for generating transgenic cotton plants that contain a dominant negative allele for an endoplasmic reticulum located protein, which provides cotton plants with lower seed storage reserve content, increased fiber yields and reduced need for macronutrients.

II. Description of the Background Art

Fiber yield enhancement using traditional plant breeding techniques has been an important objective of cotton breeding. As a result of intense breeding selection for genetic improvements in fiber yield, the genetic contribution to fiber yield and lint percent (ratio of fiber to fiber-plus-seed) has increased during the last 50 years. Transgenic technology provides new opportunities to accelerate the genetic yield gain beyond those possible using traditional methods because this technology can alter the metabolic machinery of the plant. Efforts to enhance fiber yield in cotton with transgenic technology have involved, for example, manipulating plant hormones and stress and disease tolerance. Other methods for enhancing cotton yield have been reported by Hake et al., U.S. Published Patent Application 2004/0133944 and Lauterback et al., "Yield enhancement in cotton," in *Genetic Control of Cotton Fiber and Seed Quality*, Cotton Incorporated, Cary, N.C., 2000. Transgenic technologies, such as sense suppression, antisense suppression and RNA interference methods, have been used to modify seed constituents in cotton. Seed oil modification in cotton for altering fatty acid profiles has been an active area of research. See Chapman et al., *J. Am. Oil Chemists Soc.*, 78:941-947, 2001; Liu et al., *Plant Physiol.* 129:1732-1743, 2002.

Yield enhancement technology in field crops has been an active area in plant biology research. However, in cotton the complexity and uniqueness of the harvestable product, bolls of cotton fiber, has provided special challenges. Modern chemical and biotechnological technologies for managing insect pests, combined with reduced season-length production strategies, have improved the percent boll set and the rate of sucrose utilization in fiber development in cotton. However, methods are still needed to further improve cotton plant qualities, including fiber yield enhancement, and other plant characteristics that increase the efficiency of cultivation of this important crop.

It is generally understood by those of skill in the art of plant cultivation, that cotton requires lower inputs of fertilizers than other commercial crops. This is in part due to the temporary storage in leaves of mineral nutrients needed by cotton seeds as they develop. In addition, cotton fiber is largely cellulose. Thus, input of significant amounts of macronutrients to the plant prior to anthesis and boll filling is required which results in the temporary storage of macronutrients in leaves and the resulting elevated nutrition for insect pests feeding on preanthesis cotton leaves.

Nevertheless, mineral nutrients in the soil where cotton is grown do become depleted, and the application of commercial fertilizers is eventually required, particularly where cotton is grown in rotation with other commercial crops such as corn, ground nuts, cassaya, millet, rice and grain legumes. In developing countries resources needed to purchase fertilizer could be diverted from those available for essential human needs such as shelter, medicine, food and education.

Advances in agricultural technology have provided new plant varieties that require reduced tillage of the soil. However, reduced tillage also results in the reduced availability of macronutrients. This is particularly true where plant debris or litter remaining after harvest is not tilled or plowed back into the soil. A recent study has shown that approximately 46% of the nitrogen from cotton litter is released into the soil during the four month period after it is incorporated or plowed under in a field. Only about 19% is released when no-till methods are used. (See Lachnicht et al., 2004). Thus, application of increased amounts of fertilizer or elevated soil nutrient availability is required for no till crop rotations.

The availability of new varieties of cotton that require lower amounts of fertilizer would further improve the efficiency of cultivation methods, particularly in developing countries where resources are scarce. Thus, new varieties with traits that provide reduced levels of stored mineral macronutrients are desired.

The need for the addition of the macronutrient phosphorous back to the soil results in part from the accumulation of phytate (phytic acid or inositol-hexaphosphoric acid) in seed. In plants phytate is metabolized into inorganic phosphate, which is utilized in energy transfer. However, non-ruminant animals do not efficiently metabolize phytate. Phytates from seeds used in animal feeds can contaminate manure and be leached into streams, lakes and oceans where microbial degradation of the compound releases phosphate, which in turn can lead to algal growth and eutrification (anaerobisis, oxygen deprivation) of bodies of water. (See Ferber 2004; Leigh 2004.) Phosphate and nitrogen runoff from agriculture in the central United States into rivers and the Gulf of Mexico is recognized as a major source of eutrification of the fish habitat in those bodies. Thus, plants and methods for producing those plants with decreased storage of phosphorus in the form of phytate are desired.

SUMMARY OF THE INVENTION

Accordingly, this invention relates to a method of generating cotton plants with improved qualities, such as increased fiber yield and reduced nutrient requirements. In one embodiment the invention provides a method for introducing a transgene, for example a chimeric gene, into cotton plants to increase the supply of nutrients available for plant vegetative growth and development of plant products.

In a further embodiment a chimeric gene is introduced into cotton plants to increase the supply of sucrose available for vegetative growth and for development of fiber during the boll-filling phase of growth. In one preferred embodiment the chimeric gene comprises a negative dominant allele of a native gene that provides a function which directly effects production of a desired product such as fiber yield and/or specific nutrient requirements in a plant.

In another embodiment, a chimeric gene is introduced into cotton plants to decrease the storage of protein, phytate and/or mineral nutrients such as nitrogen, phosphorous and potassium. In this embodiment the transgenic plants require less nutrients from the soil. Moreover, more nutrients will be available for sustained fiber development and for vegetative growth of the plant.

In another embodiment, the invention provides a method of increasing fiber yield in a cotton plant that comprises inserting, into a cell of the plant, a transgene, the expression of which reduces the activity of one or more enzymes that function in oil production in cottonseed, and regenerating a whole cotton plant from the transformed cell. In preferred embodiments, the transgene comprises a nucleic acid sequence coding for an enzyme selected from the group consisting of carbonic anhydrase, acetyl-CoA carboxylase, fatty acid desaturase, lysophosphatidic acid acyltransferase, diacylglycerol acyltransferase, phospholipid: diacylglycerol acyltransferase and β-keto-acyl carrier protein synthase II. Most preferred transgenes code for dominant negative alleles of a gene encoding an endoplasmic reticulum located protein, for example a mutant delta-12 fatty acid desaturase (FAD2) gene. A mutant canFAD2 gene of canola is most preferred.

In preferred embodiments, the transgene is operably linked to a seed-specific promoter that has negligible to nil expression in anthers and pollen, most preferably the α-globulin promoter of cotton. In further embodiments the linkage between the transgene and the promoter is convertible from an inoperable to an operable linkage by the action of a gene switch.

Another preferred embodiment comprises a method of increasing fiber yield, which comprises inserting into a cell of a cotton plant, a chimeric gene comprising the α-globulin promoter of cotton and a nucleic acid sequence coding for a mutant canola FAD2 gene, expression of which reduces expression or activity of enzymes of oil production in cottonseed, and regenerating a whole plant from the transformed cell.

In another preferred embodiment, a series of DNA elements that allow an exogenous stimulus to turn on expression of a transgene in a plant cell where expression of that transgene reduces the activity of one or more enzymes that function to regulate seed-oil and/or protein production or to reduce storage of macronutrients in seed are inserted into a plant cell.

In a further preferred embodiment, whole plants are regenerated from the transformed plant cells. Plants having a gene switch system which controls expression of a gene that suppresses seed-oil, protein, phytate and/or macronutrients allows a plant breeder or farmer to activate expression of this desired trait only in a plant generation where commercial fiber production is desired, thus maximizing the metabolic and nutrient resources available for plant fiber production. This embodiment finds particular use where the transgene introduced to provide increased nutrient resources for fiber production causes undesired effects on the properties and germination ability of seed. Thus, a crop of cotton can be grown to produce seed, those seed can be planted and resulting plants grown to produce a generation of plants for fiber production. The transgene or transgenes for increasing nutrient resources are turned on by the application of an exogenous stimulus by gene switches that are known to those of skill in the art.

Thus, in an additional preferred embodiment the present invention relates to a system for suppressing the accumulation of seed-oil, for example, triacylglycerol, in cotton seeds by introducing a transgene into a plant suppresses the accumulation of seed-oil where expression of that gene is controlled by an exogenous gene switch. In additional embodiments the transgene suppresses the accumulation of stored protein in cotton seeds and/or the accumulation of phytate and inorganic phosphorous in cotton seeds. It is contemplated that the genes used to produce these quality enhanced plants may be different, or they may be the same. That is, it is contemplated that in some embodiments the introduction of a single transgene will simultaneously suppress the accumulation of seed-oil, proteins and/or phytate. That transgene may also suppress storage of macronutrients in seed. In other embodiments different transgenes may be used to achieve this desired result.

Additional preferred embodiments provide plants produced according to the methods described above.

DETAILED DESCRIPTION OF THE INVENTION

Figure 1:
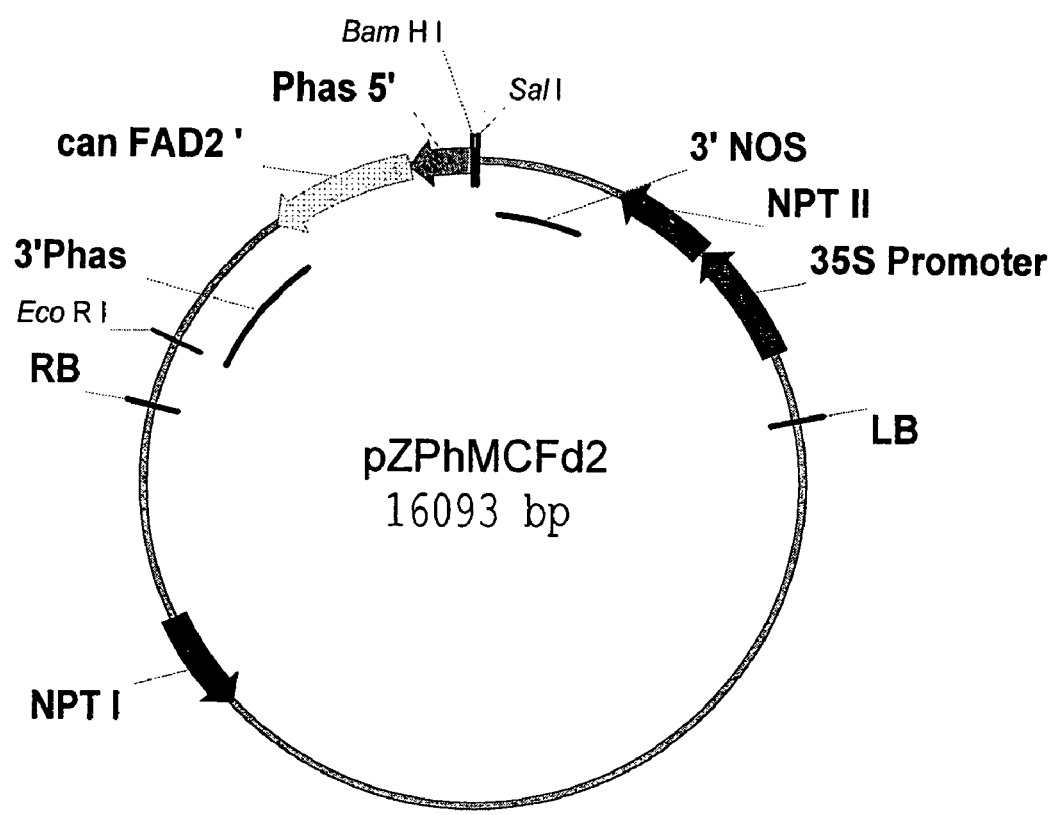
FIG. 1 is a diagram of a binary vector, pZPhMCFd2, for use in cotton transformations, which contains a mutant canola FAD2 gene.

Cotton seeds typically are composed of about 3.5% w/w starch, 20% w/w oil and 20% w/w protein. Stored seed-oil is predominantly (97%) triacylglycerol (TAG) derived from linoleic (18:2), palmitic (16:0) and oleic (18:1) fatty acids. The present inventors have discovered that the resources needed for the biosynthesis of oil and protein in cotton, including sucrose, reduce the supply of transportable carbon available for biosynthesis of fiber and for additional vegetative growth. Without being limited by any theory as to how reducing oil and protein limits biosynthesis of fiber and additional growth, this is thought to occur because phloem-transported carbon ultimately is the primary metabolic resource for seed-oil (primarily TAG), protein and cotton fibers, and because utilization of sucrose for production of fiber, protein and oil coincide temporally on a whole plant level.

Although cumulative cellulose deposition within a boll precedes peak oil and protein accumulation by approximately 15 days; oil, protein and cellulose accumulate concomitantly in the whole plant. When compared with the biosynthesis of cellulose from sucrose, the seed oil TAG biosynthetic pathway and protein biosynthetic pathway are energetically inefficient. As a result of relative sucrose depletion during boll maturation, new vegetative tissue and fiber development ceases during the period referred to as "cutout" (Kerby et al., 1993). Cutout is the stage of cotton plant growth when new monopodial nodes cease to be accumulated. Thus, fiber yield is curtailed directly, due to the diversion of sucrose to oil and protein biosynthesis, and indirectly, due to the decline in photosynthesis and soil nutrient uptake that results from the aging of the leaf and root tissues when new shoot and root production slows. Wullschleger and Oosterhuis, Crop Sci. 30:1259-1264, 1990; Kerby et al., University of California, Division of Agriculture and Natural Resources, Oakland, Calif., 1987.

In one embodiment the present invention provides a method for expanding sucrose supply for fiber development in a plant. In the method a dominant negative allele of a gene that functions to suppress TAG and protein biosynthesis in cottonseed is introduced into the plant. This gene may function to delay cutout, promote root expansion, sustain photosynthesis and sustain soil nutrient and/or water uptake or to affect other plant metabolic processes which ultimately impact expression of a desired trait, such as increased fiber production or reduced nutritional requirements. Since TAG and protein require substantially more metabolic energy to produce than cellulose and the mass of seed is greater than the mass of fiber, only a slight reduction in TAG and protein can result in an economically significant increase in fiber yield.

Extreme limitation of seed-oil and seed-protein, however, can limit seedling growth and ultimately result in poorer yield because seed-oil and seed-protein are needed in the developing cotton seedling as a source of energy, carbon and macronutrients for new growth. Thus, seed-oil and seed-protein suppression in a cultivar designed to produce more fiber preferably is controlled or regulated by a plant gene expression system which permits production of a seed crop without seed-oil suppression. The gene expression system allows these viable seeds to produce a commercial fiber crop with maximum enhancement of fiber yield. Thus, the methods of the present application allow cotton farmers to plant vigorous seed and harvest higher fiber yield, since the supplies of sucrose not diverted to TAG or storage protein would be used by the plant to produce fiber.

An important reaction in the biosynthesis of cottonseed oil, which can be targeted for down-regulation by a dominant negative allele transgene is catalyzed by Fatty Acid Desaturase (FAD). Fatty Acid Desaturase (FAD) enzymes introduce double bonds at specific positions along the saturated acyl fatty acid chain of specific fatty acids. FAD2 is an endoplasmic reticulum membrane-localized FAD that introduces a double bond into oleic acid at the delta-12-carbon position to generate linoleic acid. Fatty acids are desaturated in the endoplasmic reticulum of cottonseeds, then incorporated into TAG prior to being compartmentalized in oil bodies. Because FAD2 is co-localized in the endoplasmic reticulum with several other lipid and protein body biosynthetic enzymes, the activities of these co-localized enzymes may also be impaired, along with the activity of FAD2, by introducing a mutant FAD2, thereby reducing the efficiency of seed oil and/or protein accumulation and increasing the potential for enhanced fiber yield.

Embodiments of the present invention provide genetic methods to reduce seed protein and thereby provide additional resources for the production of cotton fiber. In some preferred embodiments these methods do not interfere with growth of the vegetative plant, the embryo, seed coat and fiber. Thus, reduction of seed protein can be achieved by the use of highly regulated, seed-specific promoters that do not express in the seed coat, anthers or fiber tissues, such as α-globulin promoter (AGP) developed by Sunilkumar, 2002; or by the use of other promoters that are known to be uniquely active during the seed maturation phase of development that is focused on reserve accumulation and the acquisition of desiccation tolerance in the embryo, such as globulins, albumins, oleosins, LEAs (late embryogenesis proteins) (Dure and Galau, 1981, Dure et al., 1981).

In one embodiment the reduction of stored protein can be achieved by down regulating enzymes responsible for amino acid biosynthesis, transport or incorporation into protein. However, these methods will most likely interfere with embryo development and fiber production. In addition, suitable enzymes must be carefully chosen such that normal seed coat function is maintained until cotton fibers mature. Suitable targets include transcriptional and post transcriptional down regulation of protein body biosynthesis and assembly.

With a reduction in seed protein body, the nutritional value for seed feeding insect pests, such as *Hemiptera* species in the *Pentatomidae* and *Miridae*, is degraded resulting in reduced preferential feeding and insect growth rates. In addition, preanthesis plants can be maintained at a reduced leaf N status relative to normal seed protein body plants such that leaf photosynthesis is not impaired by low leaf N, yet the nutritional value of cotton leaf in the diet of pest insects is impaired. To avoid a reduction in leaf photosynthesis, leaf N should be maintained above 4% N (w/w dry weight) or 2.5 SLN (g N $m^{-2}$) as calculated from Milroy and Bange 2003 and Bondada and Oosterhuis 2001. With regards to Silverleaf Whiteflies (Bi et al., 2000), reduced applications of N fertilizer resulted in no significant reduction in leaf photosynthesis until boll filling, yet provided significant reduction in the Whitefly nymph population and the number of honeydew drops per whitefly. Since high N fertilization increases canopy photosynthesis during the boll maturation period, it is logical to expect that a reduction in the N utilization in the seed should maintain canopy photosynthesis at a higher level (Milroy and Bange, 2003; Bi et al., 2000; Bondada et al., 2001).

As used in this specification, the term "gene" refers to a segment of DNA which encodes a specific protein or polypeptide, or RNA, and which may comprise a regulatory element. A "chimeric gene" is a gene constructed from parts of two or more different genes, for example a coding sequence for a protein linked to a promoter from a different gene. A "transgene" is a native or mutated gene which is artificially transferred into a cell or organism, and may include a chimeric gene. The term "fiber enhancement gene" refers to any gene the expression of which can result in enhanced fiber production in the bolls of cotton plants expressing the gene. The term "dominant negative allele" generally refers to a mutant or native gene that, when expressed, interferes with the function of a normal gene product or a normal protein complex.

Dominant negative alleles or traits are ones that modify the primary structure of a protein to introduce physical changes in the structure of a protein that affect an entire system of enzymes that work together. As the term is used with respect to this invention, any gene that can interfere with an endogenous gene product or group of gene products that work together, through physical/structural changes, is considered to have a dominant negative allelic effect and to be a dominant negative allele, whether actually mutated or not.

Dominant negative allele proteins include proteins with similar amino acid sequences to an endogenous protein, but which are rendered non-functional or less functional by a change or changes in the amino acid sequence. When the dominant negative allele interacts with the complex which the corresponding endogenous protein interacts, the efficiency of the complex is reduced. Thus, the term includes proteins and fragments thereof found in nature that are not native to the plant in which they are expressed, but which function in the manner of a dominant negative allele due to their lack of homology with the native proteins, when present. Also included are proteins encoded by nucleic acid sequences that are modified using the techniques of molecular biology to produce dominant negative alleles.

A dominant negative allele can be identified as a mutation or change in an active site of a protein, for example an enzyme binding site or a receptor ligand binding site of a protein. An addition of a binding site or other domain or mutation which makes the affected complex non-dissociable and non-functional also can be identified as a dominant negative allele according to an embodiment of the present invention. Thus, expression of the "dominant negative allele" interferes with the function of an endogenous gene product or one or more of a homomeric enzyme, a heteromeric enzyme or a physical region of enzymatic activity.

Dominant negative alleles of proteins associated with lipid biosynthesis and storage may be used according to the present invention as fiber enhancement genes. Expression of heterologous genes that provide a dominant negative allelic effect on fatty acid biosynthesis can reduce oil production and enhance fiber production. These genes can include those that synthesize unusual fatty acids not normally found in cotton, such as short chain fatty acids, medium-chain fatty acids, hydroxy fatty acids, epoxy fatty acids, conjugated fatty acids or acetylenic fatty acids. Expression of these genes in a heterologous host, such as cotton, can impact total oil accumulation by making gene products which interact with endogenous protein machinery and reduce the optimal synthesis and packaging of seed oil. The seed-specific synthesis of any protein, whether an enzyme or a structural protein, that interferes with the proper synthesis, assembly and packaging of seed oil (consistent with a dominant negative allelic effect) will provide the plants with additional resources to allocate to fiber production.

Fiber enhancement genes include genes that exhibit a dominant negative allelic effect that eliminates, blocks, interferes with, prevents, or otherwise reduces the biosynthesis of seed oil in the cotton plant. Fiber enhancement genes may include, for example, dominant negative alleles of carbonic anhydrase, acetyl-CoA carboxylase (ACCase), lysophosphatidic acid acyltransferase, diacylglycerol acyltransferase, phospholipid: diacylglycerol acyltransferase (PDAT), β-keto-acyl carrier protein synthase II (KASII), caleosin, oleosin and others.

In preferred embodiments of this invention, an FAD2 gene that acts as a dominant negative allele to disrupt the endoplasmic reticulum-localized metabolic processes is used to construct a chimeric gene that can be inserted as a transgene into a cotton plant. For example, an FAD2 allelic gene that converts oleic acid to linoleic acid and thereby alters production and incorporation of TAG in lipid bodies can be used. Due to the physical proximity of several lipid biosynthetic complexes in the endoplasmic reticulum, dominant negative allele FAD2 genes can operate to eliminate or reduce the amount or activity of more than one lipid biosynthetic enzyme. Modifications to the secondary structure and/or tertiary structure of an enzyme or other protein, created by one or more dominant negative alleles, can alter the quaternary structure of a physically associated group of enzymes and thereby impair the function of the physically associated enzymes, including enzymes important to lipid and protein biosynthesis and storage.

In further embodiments of the present invention, enzymes involved in seed oil production, such as carbonic anhydrase, ACCase, lysophosphatidic acid acyltransferase, diacylglycerol acyltransferase, PDAT, KASII, caleosin, oleosin and others as discussed above are inserted into plant cells. Plants transgenic for a preferred mutant FAD2 gene or another gene, as a dominant negative allele, produce increased fiber.

Nucleic acids encoding fatty acid desaturase enzymes are known to those of skill in the art. For example, U.S. Pat. No. 6,372,965 discloses the sequences of cDNAs that encode microsomal FAD2 from *Arabidopsis thaliana*, *Brassica napus*, soybean (*Glycine max*), corn (*Zea mays*) and castor (*Ricinus communis*). Allelic variants of these genes can be identified readily in native cotton plants using techniques known to those of skill in the art such as nucleic hybridization. Allelic variants also can be generated by either random or site-directed mutagenesis using strategies known to those of skill in the art of plant molecular biology. Dominant negative alleles can be identified in either transformed T0 embryogenic tissue, T1 seed produced from T0 plants or subsequent seed generations by selecting transformed lines with either impaired lipid biosynthetic enzymes or altered lipid profiles and with reduced seed oil content. Strategies for identifying dominant negative alleles are known to those skilled in the art, which can be easily adapted to optimize the embodiments of the present invention.

Preferably, the transgenes (chimeric genes) for use in the inventive methods will have seed-specific promoters that have negligible activity in non-seed tissue to allow full pollen viability, minimize the chance for metabolic disruption in non-seed tissues and lessen the metabolic cost associated with constitutive expression or over-expression of the transgenic protein. Because TAG is required for pollen viability, transgenes preferably are expressed in pollen only at low levels and most preferably are not active or have negligible activity in pollen so as not to affect pollen viability. The alpha globulin promoter of cotton is most preferred. See Sunilkumar et al., *Transgenic Res.* 11:347-359, 2002; Hseih and Huang, *Plant Physiology* 136:3427-3434, 2004.

Any plant-active seed-specific promoter useful to express the transgene in seed tissue of the plant may be used, however, such as constitutive or inducible promoters. Many such promoters are known in the art and can be adapted for use by the skilled artisan. Typically, a promoter is located in the 5' region of a gene, proximal to the transcriptional start site of a structural gene. A plant-active promoter can be of viral, bacterial, fungal, animal, or plant origin. The term "plant-active promoter" refers to a DNA sequence that directs the transcription of an operably linked DNA sequence in a plant cell.

A "constitutive promoter" is a plant-active promoter that affects the transcription of a DNA sequence, irrespective of temporal, developmental, hormonal, chemical or environmental conditions, for example in the absence of a traditional ligand. An "inducible promoter" is any promoter that is activated by the application of, or exposure to, an external stimulus. The external stimulus can be chemical, environmental (physical), or biological in nature. An "enhancer" is a DNA regulatory element that can increase the efficiency of transcription or confer tissue specificity. An enhancer may be located at any distance or orientation relative to the start site of transcription and is optionally used with the transgenes of this invention.

The coding sequence and the promoter of a chimeric gene are operably linked if they are on the same strand of DNA, in the same orientation, and located relative to one another such that the promoter is capable of directing transcription of the coding sequence. The chimeric transgene also may have an intervening or blocking DNA sequence within the promoter or between the promoter and the coding sequence, which prevents the coding sequence from being expressed. The blocking sequence is a DNA sequence that blocks the promoter's activity with respect to expression of the coding sequence of the chimeric gene. A specific excision sequence is a DNA sequence that is recognized by a site-specific recombinase, which is an enzyme that removes or otherwise alters DNA between specific excision sequences. The term "gene switch" refers to a set of genetic elements that when treated with appropriate external conditions can cause a promoter and coding sequence to be either operably linked or operably unlinked, as is generally understood in the art.

An option for regulation of the transgene in transgenic plants produced by the methods of this invention is to place activation of the transgene under the control of a system that is activated by application of an external stimulus. To effect this regulation, the fiber enhancement gene may be operably linked to an inducible promoter that can respond to an external stimulus, for example the promoter from the ACE1 system, which responds to copper; the promoter of the maize intron 2 gene, which responds to benzenesulfonamide herbicide safeners; the promoter of the Tet repressor from Tn10; the phosphate-deficiency responsive promoter from a phosphate-starvation responsive beta-glucosidase gene from *Arabidopsis*; the ethanol-inducible promoter of *Apergillus nidulans*; the synthetic promoter containing a 235 bp sulfur deficiency response element from a soybean β-conglycinin gene linked to a 35S core promoter sequence or any other suitable promoter known to those of skill in the art of plant molecular biology.

Inducible promoters that respond to an inducing agent to which plants do not normally respond are particularly useful; however, any inducible plant-active promoter may be used in this invention. An exemplary preferred inducible promoter is the inducible promoter from a steroid hormone gene, the transcriptional activity of which is induced by a glucocorticosteroid hormone or the chimeric transcription activator, XVE, for use in an estrogen receptor-based inducible plant expression system activated by estradiol. See Zuo et al., *Nat. Biotechnol.* 19:157-161, 2001, the disclosures of which are hereby incorporated by reference. Using this type of system, the transgenic plant or its developing seed is treated with the specific activator when activation of the fiber enhancing gene is desired. The chimeric transgene is expressed as long as the activating chemical is present in the cells of the plant. Therefore, activation of the transgene generates transient pools of sucrose in the resultant cottonseed that are available to stimulate production of commercially valuable cotton fibers.

By controlling the expression of genes that affect the seed-oil and/or protein content of a seed, it is possible to grow plants under one set of conditions or in one environment where it is advantageous to not express the transgene in the seed, then to alter the environment directly, or indirectly by moving the plant or its seed to another set of conditions or another environment where the expression of the transgene is desired.

Seed-specific promoters are preferred. The term "seed-specific promoter" refers to any plant-active promoter that is either active exclusively in the plant seed or active in the plant seed and to a lesser degree other plant tissues. A seed-specific promoter may be a promoter native to seed tissue or may comprise a core plant-active promoter of plant, viral, bacterial, fungal, or animal origin with a seed tissue-preferred regulatory region that directs a higher level of transcription of an associated gene in seed tissues than in some or all other tissues of a plant. Seed-specific promoters also can include promoters with one or more enhancer elements that confer upon the promoter (of any origin) specificity for seed tissue expression. One such promoter is the phaseolin promoter from bean. An especially preferred promoter is the recently identified α-globulin promoter (AGP) from cotton. See Sunilkumar et al., *Transgenic Res.* 11:347-359, 2002, the disclosures of which are hereby incorporated by reference.

Expression of the transgene may create too little or too much suppression of oil biosynthesis for optimal fiber enhancing effect. Thus, it may be necessary in some embodiments of the invention to perform multiple insertion events. Adjustment of expression levels by this method by adjusting the promoter and/or enhancer used is considered routine to those of skill in plant molecular biology and is contemplated for use with the invention.

If suppression at multiple sites in the TAG biosynthetic pathway are desired to achieve maximum fiber yield enhancement while maintaining a supply of fatty acids for normal seed development, dominant negative allele inhibition sequences can be operably linked to one promoter according to known methods. See, for example, Abbott et al., *Plant Physiol.* 128:844-853, 2002. To achieve the highest level of fiber yield enhancement from cottonseed oil suppression while maintaining sufficient seed vigor, expression of the transgene preferably is regulated in various generations of plants that are produced for planting seed or for fiber production. A suitable method is to regulate gene expression using an excisable block between a late embryogenesis activated (LEA) promoter and a seed germination inhibitor. See Oliver et al., U.S. Pat. No. 5,723,765, the disclosure of which is hereby incorporated by reference in its entirety. By replacing the LEA promoter with the AGP promoter and the seed germination inhibitor with dominant negative allele genetic elements that inhibit TAG biosynthesis, this mechanism may be used in an embodiment of the invention to generate high vigor cotton seed which produce plants with enhanced fiber production. Seed produced from these fiber production plants are viable but low in TAG and thus have reduced capacity to establish a seedling under field conditions.

Cotton plants that may benefit most from the advantages conferred by the methods of this invention are *Gossypium hirsutum, G. barbadense* and *G. arboreum*, because these species produce oil, protein and commercially valuable fiber. Especially preferred varieties and hybrids include those that generate and retain to anthesis an excess of fruiting sites, but subsequently either abort or only partially mature some of these fruiting sites due to a limited supply of transportable carbon in the phloem. Because there are multiple advantages from reducing transportable carbon use for oil/protein biosynthesis and storage, most cotton fiber production systems will benefit. These benefits include enhanced nutrient and water uptake and enhanced tolerance of stress from sources such as soil-borne pathogens, nematodes, compacted soils, acid soils, foliar diseases, infertile soils and insect damage, as well as fiber yield enhancement.

Methods for inserting foreign genes into the nuclear genome of plants are well known to skilled persons in this art. Numerous plant tissues can be used to prepare transgenic cotton plants, including hypocotyl, petiole, root, cotyledon, pollen, and others. Sunilkumar and Rathore, *Mol. Breeding* 8:37-52, 2001, the disclosures of which are hereby incorporated by reference, discuss advantageous methods for DNA transfer in cotton. However, any suitable transformation method known in the art can be used with the invention. Insertion methods generally fall into two categories: physical methods such as biolistics, whiskers and electroporation, and biological methods that employ *Agrobacterium tumefaciens* or a virus to enhance DNA insertion.

Once a desired dominant negative allele gene for fiber enhancement has been inserted into cotton, testing for fiber yield enhancement may be conducted in the plants using traditional methods known in the art of trait selection for transformed and regenerated cotton plants. A method for confirming the expression of the desired trait of fiber enhancement may include direct measurement of fiber in plants with and without the transgene. Alternatively, DNA, RNA, or protein selection for reduced TAG concentration may be measured in callus or regenerated tissue from the plant. TAG concentration is determined for selection in the T0 embryonic tissue, T1 seed (grown on the T0 plant) and/or subsequent seed generations, since the oil suppression trait will be expressed only in seed if a seed-specific promoter is used as is preferred. The resulting fiber yield enhancement provided by the transgenic trait according to the invention may be evaluated in elite germplasm, such as the elite varieties DeltaPEARL, DP 491, DP 444 BG/RR, DP 432 RR and the elite hybrid DPX03N110.

Methods for assay of TAG and other oils in plants are well known in the art. Any of these methods are suitable for assaying seed oil of plants produced according to the methods of this invention. The desired change in FAD2 expression can be determined by the proportional increase in oleic acid and compensatory decrease in linoleic acid in the seed oil. This can be determined by gas chromatographic analysis of fatty acid methyl esters produced from the total extractable seed lipids according to the methods of, for example, Chapman et al., *J. Am. Oil Chemists Soc.* 78:941-947, 2001. Seed oil content can be estimated gravimetrically prior to transmethylation.

In preferred methods, the plant-active promoter used to drive the expression of the fiber enhancing gene is a seed-specific promoter, most preferably the cotton α-globulin promoter (AGP), operably linked to a DNA sequence coding for a mutant FAD2 protein in a synthetic construct. An alternative inducible plant-active promoter used to drive the expression of the site-specific recombinase gene preferably is either the ecdysone or estrogen receptor-based inducible plant expression system. A preferred ecdysone inducible plant expression and recombinase/excision sequence system for use with the inventive method is the GVE system described in Padidam et al., *Transgenic Res.* 12:101-109, 2003. and bacteriophage CRE/LOX system, wherein the CRE protein performs site-specific recombination of DNA at LOX sites as described in Sauer, U.S. Pat. No. 4,959,317, the disclosures of which are hereby incorporated by reference. The preferred fiber enhancing gene is the dominant negative allele canola FAD2 gene.

Once the desired transgene for protein body or phytate suppression has been transformed into cotton, testing for seed nutrient content and fiber yield enhancement is conducted in plants using traditional methods known in the art of trait selection for transformed and regenerated cotton plants. A method for confirming the expression of the desired trait may include direct measurement of the protein, phytate and phosphorous content of seeds with and without the transgene. Alternatively, DNA, RNA, or protein selection for reduced protein body, phytate or phosphorus concentration may be measured in callus or regenerated tissue from the plant.

Protein body and P concentration is determined for selection in the T1 and/or subsequent generations, since the protein body and phytate suppression traits will be expressed only in seed if a seed-specific promoter is used as is preferred. The resulting fiber nutrient efficiency and fiber yield enhancement from transgenesis according to the invention is best evaluated in transgenic elite germplasm. Methods for assay of protein, protein body and phytate as well as N, P and K in plants are well known in the art. Any of these methods are suitable for assay in conjunction with this invention. A preferred method is determination of total nitrogen by AOAC 4.2.08 from the Official Methods of Analysis of AOAC International, 17th Edition, 1998; and total P and K by SW-6010B from the USEPA, SW-846, Test Methods for Evaluating Solid Wastes, Physical/Chemical Methods, 3rd Ed. Current Revision.

Due to the simultaneous storage of both oil bodies and protein bodies in the embryo, a strategy for suppression of both oil and protein in seed is the suppression of seed development using transcription factors. Mutations in the "leafy cotyledon" 1 (LEC1) transcription factor disrupt normal embryo development and maturation in *Arabidopsis* affecting both embryo morphogenesis and reserve accumulation (Kwong et al., 2003). It may be possible to down-regulate APETALA (Jofuku et al., 2005; Ohto et al., 2005) and/or LEC1 in cotton embryos specifically during seed maturation using a cottonseed storage protein promoter (alpha-globulin, Sunilkumar et al., 2002) thereby affecting only the stage of reserve accumulation in developing seeds. It is likely that this strategy will disrupt the program of embryogenesis such that viable seeds will not be recovered, necessitating the use of a gene switch as discussed above to turn on the transcription factor only in the plant generation used to produce commercial quantities of fiber.

Due to the role of the endoplasmic reticulum in biosynthesis and assembly of both oil bodies and protein bodies, a preferred method to achieve a simultaneous reduction in oil, N, P and K in cotton seeds is a dominant negative mutation for an essential gene that functions in the endoplasmic reticulum. ER proteins are synthesized co-translationally (mostly), glycosylated and processed in the ER, so any proteins that participate in this process may be targets for suppression by dominant negative mutation of ER function (and hence oil and protein body formation). These include proteins of, or associated with, the ER-translocator, the glycosyltransferase that transfers high mannose side chains to ER glycoproteins, the suite of molecular chaperones in the ER, including BiP (HSP70), peptidyl-prolyl isomerase (PPI), calnexin, calreticulin, and protein disulfide isomerase (PDI), the proteins associated with ER trafficking machinery, including the multitude of monomeric GTP-binding proteins that function in these pathways, the RABs, ARFs (and ARF-like proteins), dynamins, and SNAREs. Depending on the selection of the protein target to suppress by a dominant negative mutation, either protein bodies or oil bodies may be preferentially reduced. In embodiments where either seed oil or seed protein are desired, this may be a preferred outcome. A dominant negative mutation that preferentially disrupts protein bodies, while leaving oil bodies essentially intact, would be desirable in fertilizer-limited markets that place a high value on cotton seed oil but low value on cotton seed meal.

Figure 12:
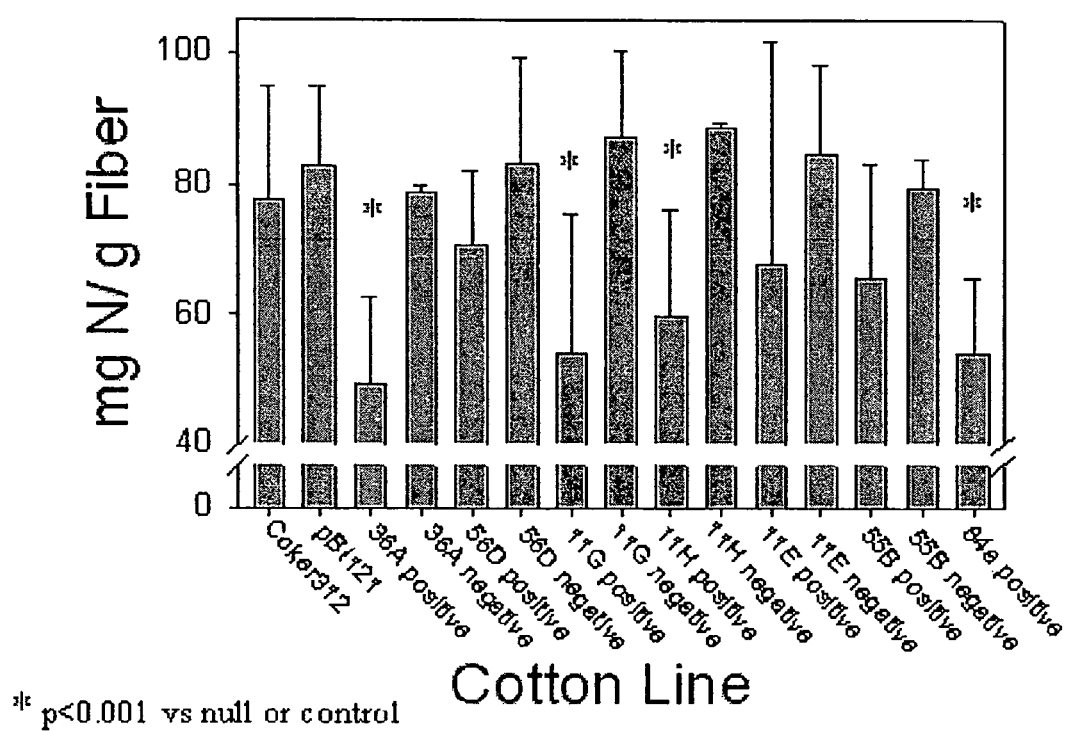
FIG. 12 provides total seed nitrogen (N) per mass of fiber harvested from FAD2 PCR positive and PCR negative T1 plants.
Figure 13:
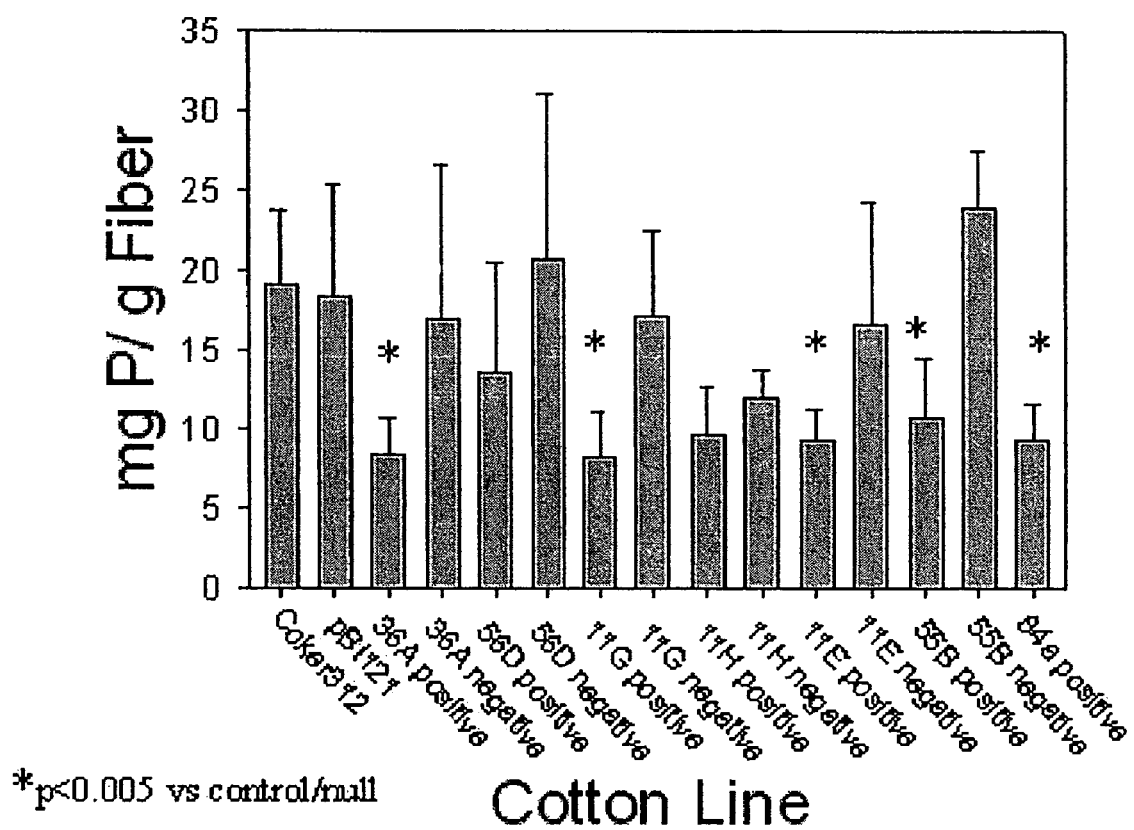
FIG. 13 provides total seed phosphorus (P) per mass of fiber harvested from FAD2 PCR positive and PCR negative T1 plants.
Figure 14:
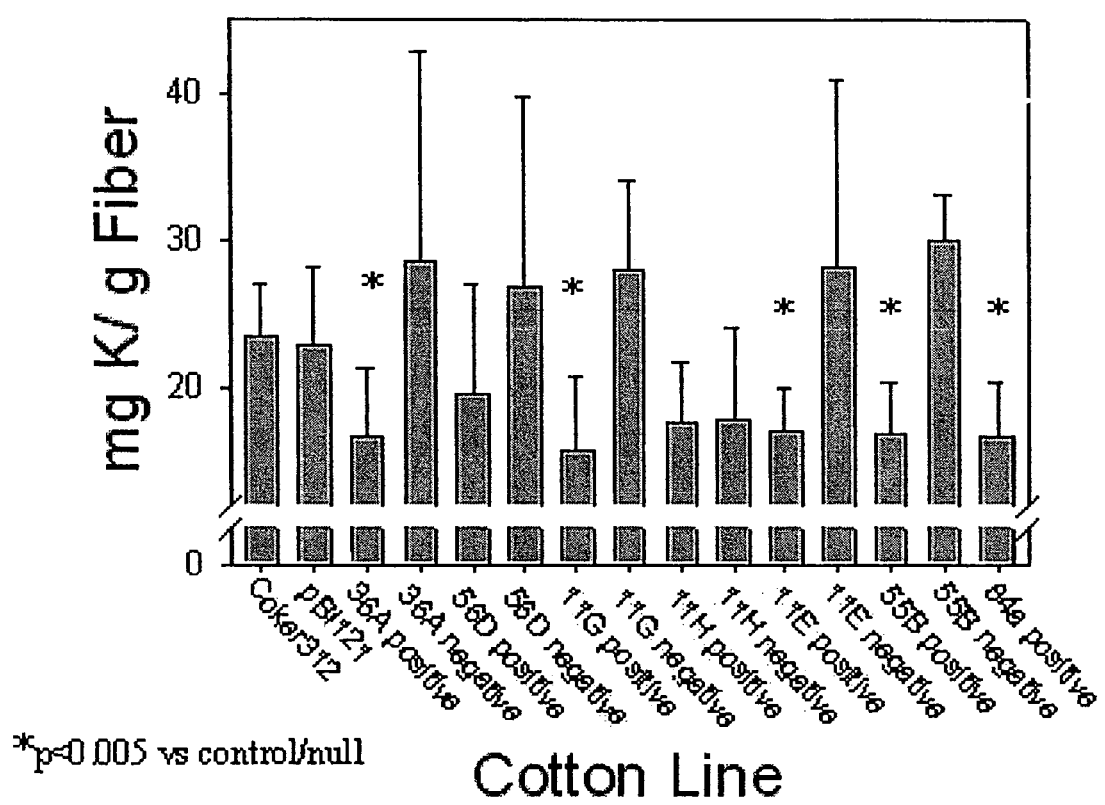
FIG. 14 provides total seed potassium (K) per mass of fiber harvested from FAD2 PCR positive and PCR negative T1 plants.

Interference with the function of any of these proteins will conceivably disrupt the correct function of the endomembrane system and result in poor efficiency of N, P and K reserve accumulation. Although not wishing to be bound by any theory of how embodiments of the present achieve the desired results, the dominant negative mutant Canola FAD2 (an ER-bound protein) appears to interfere with the accumulation of N, P and K reserve accumulation as shown in FIGS. 12-14 and Table VII, presumably by interfering with ER function. Thus, additional ER-bound enzymes involved in triacylglycerol (TAG) synthesis may be useful as targets that could disrupt packing of oil and protein bodies. These include the multitude of acyltransferases (G-3PAT, LPAAT, DGAT, PDAT, etc) that cooperate to place acyl groups on the glycerol backbone of TAGs.

The invention is further illustrated by the following examples which are not intended to be limiting in any way.

EXAMPLES

Example 1

Production of Transgenic Cotton Plants Expressing a Mutant Canola FAD2 Gene

Plants were produced using the following methods. Cotyledon pieces (approximately 3 mm$^2$) were excised from 7-14 day old cotton (*Gossypium hirsutum*, L., cv. Coker312) seedlings germinated aseptically according to known methods. See Thomas et al., *Plant Cell Reports* 14:758-762, 1995; Trolinder and Goodin, *Plant Cell Tissue Org. Culture* 12:43-53, 1988. Seedlings were grown at 30° under a 14 hour photoperiod, 60 μmol/s/m$^2$.

Cotton explants were co-cultivated with 6×10$^8$ cells/mL *Agrobacterium tumefaciens* LBA4404, harboring the binary vector pBI121 for vector-only control experiments, or pZPhMCFd2 for fatty acid modification. Transgenic plants were regenerated by somatic embryogenesis. pZPHMCFd2, a binary vector, contains the Ti-plasmid left and right border (LB, RB) inverted repeat sequences for integration into cotton genomic DNA. The T-DNA segment harbors the selectable marker neomycin phosphotransferase (NTPII) regulated by the CaMV35S promoter, conferring kanamycin resistance to the transgenic plant cells. In addition, a fad2 suppression cassette was inserted into the T-DNA segment between unique BamHI and EcoRI sites. This cassette contains a nonfunctional canola mutant fad2 allele (2860 bp) subcloned between the 5' and 3' flanking regions of the phaseolin gene. Expression of this gene was regulated by the phaseolin promoter (Phas 5') and terminator regions (3' Phas).

Figure 2:
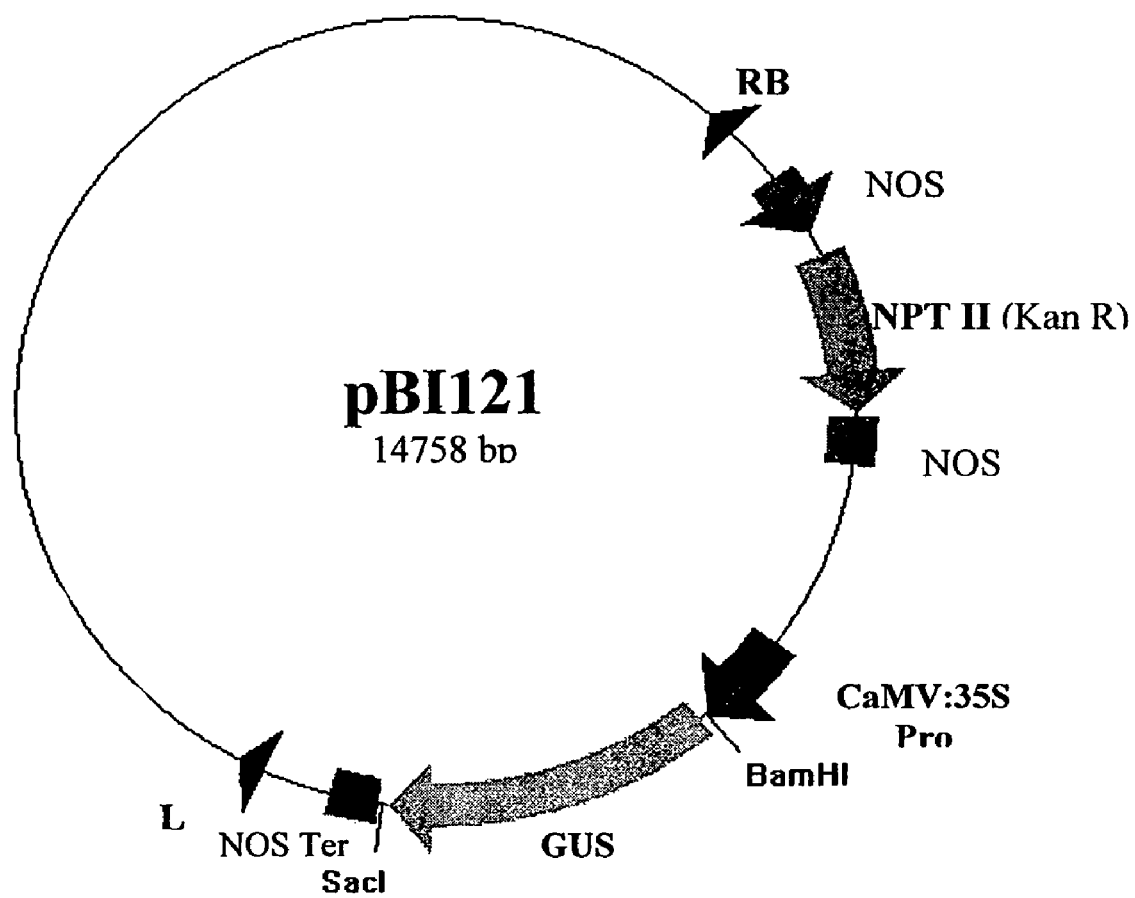
FIG. 2 is a diagram of a binary vector without a FAD2 sequence, designated pBI121-1.

The pZPhMCFd2 binary vector was introduced into *Agrobacterium tumefaciens* (strain LBA4404) by electroporation and maintained with kanamycin selection conferred by NPTII expression. See FIG. 1. FIG. 2 is a diagram of a control vector designated as pBI121, which lacks an FAD-coding sequence. See Chapman et al., *J. Am. Oil Chem. Soc.* 78:941-947, 2001. The NPTII gene is under the regulation of the nopaline synthetase (NOS) promoter and conveys kanamycin resistance. The glucoronidase (GUS) gene is under the control of the cauliflower mosaic virus (CaMV) 35S promoter. Left (LB) and right (RB) T-DNA burden sequences facilitate incorporation into the host genome. Control transgenic cotton plants were produced using this vector by known methods. See Firoozabady et al., *Plant. Mol. Biol.* 10:105-116, 1987; Umbeck et al., *Plants Biotechnol.* 5:263-266, 1987; Thomas et al., *Plant Cell Reports* 14:758-762, 1995.

Briefly, cotton cotyledon explants were placed in co-cultivation medium (MS salts, see Murashige and Skoog, *Physiol. Plant.*, 15:473-497, 1962, which contains 1.5% w/v sucrose and 40 μM acetosyringone in 2 mM MES-NaOH, pH 5.5) along with an equal volume of *Agrobacterium* cell suspension. This mixture was placed under vacuum (25C Hg) for 8 minutes, and equilibrated to 25° C. in a water bath for an additional 75 minutes. Explants then were blotted on sterile filter paper and placed on G1 medium (MS salts with 3% w/v glucose) for 3 days at 25° C. The explants then were transferred to G2 medium (G1 medium also containing 100 mg/L inositol, 1 μM thiamine, 25 μM 6-(g-g-dimethylallylamidopyrine (21P), 0.5 μM napthaleneacetic acid (NAA), 0.2% w/v Phytagel (Sigma) 400 mg/L carbenicillin and 50 mg/L kanamycin at pH 5.8). The transformed calli were subcultured every 2-4 weeks to fresh G2 medium. Mock transformations (co-cultivation of explants with *Agrobacterium* that contained no binary vector) were conducted in each case to verify that selection procedures were adequate. After 2-3 months, proliferating transgenic calli were transferred to a modified MSOB medium (G1 medium containing B-5 vitamins, 1.9 mM potassium nitrate, 100 mg/L inositol, 0.2% Phytagel, 200 mg/L carbenicillin and 50 mg/L kanamycin, pH 5.8.

Developing embryos were recovered after 6-8 weeks and placed on MSOB medium without antibiotics. Elongated embryos were transferred to MS3 medium (MS salts containing 0.4 μM thiamine-HCl, 0.5 μM pyridoxine-HCl, 0.8 μM nicotinic acid, 0.8 g/L Phytagel™ and 4 g/L agar, pH 5.8) for root formation. Small plantlets were propagated clonally according to known methods (Hemphill et al., *Plant Cell Rep.* 17:273-278, 1998), or transferred to soil, hardened off, then transferred to glasshouse conditions (14 hour photoperiod, supplemented with high intensity Na- and Hg-vapor lamps when necessary, 35° C. day/25° C. night) for production of flowers and bolls. Plants were fertilized biweekly with a dilute solution of Miracle Gro®, and flower production was stimulated with Super Bloom® when necessary. Flowers were selfed and tagged at anthesis. Progress of boll development was monitored daily. Any male sterile primary tranformants (less than 5% of plants) were hand pollinated with Coker312 wild type pollen to obtain viable progeny.

Seeds from 43 individual primary transformants (see Example 1) were analyzed and scored for oleic acid percentage. Whole cottonseeds (pooled 8-seed batches or single seeds) were frozen in liquid nitrogen and ground to a fine powder with a mortar and pestle. Ground seeds were extracted with hexane. Aliquots of these hexane extracts were dried under flowing nitrogen and transesterified with acidic methanol essentially as described by Christie, *Lipid Analysis*, Second Edition, Pergammon Press, New York, pp 52-54, 1982, except that the $KHCO_3$ wash and $Na_2SO_4$ drying steps were omitted. Fatty acid methyl esters were analyzed by gas chromatography (GC) and quantified by flame ionization detection (FID) essentially as described by Chapman and Trelease, *J. Cell Biol.* 115:995-1007, 1991, except that a 30 m (0.25 mm i.d.) DB-23 (J&W Scientific) capillary column was employed for separation and the oven temperature was 200° C. Eight lines were selected and analyzed for total lipid content (more than 95% triacylglycerols) by gravimetric analysis of the total lipid extract. The methods for this analysis were modified from Chapman and Moore, *Arch. Biochem. Biophys.* 301:21-33, 1993.

Figure 5:
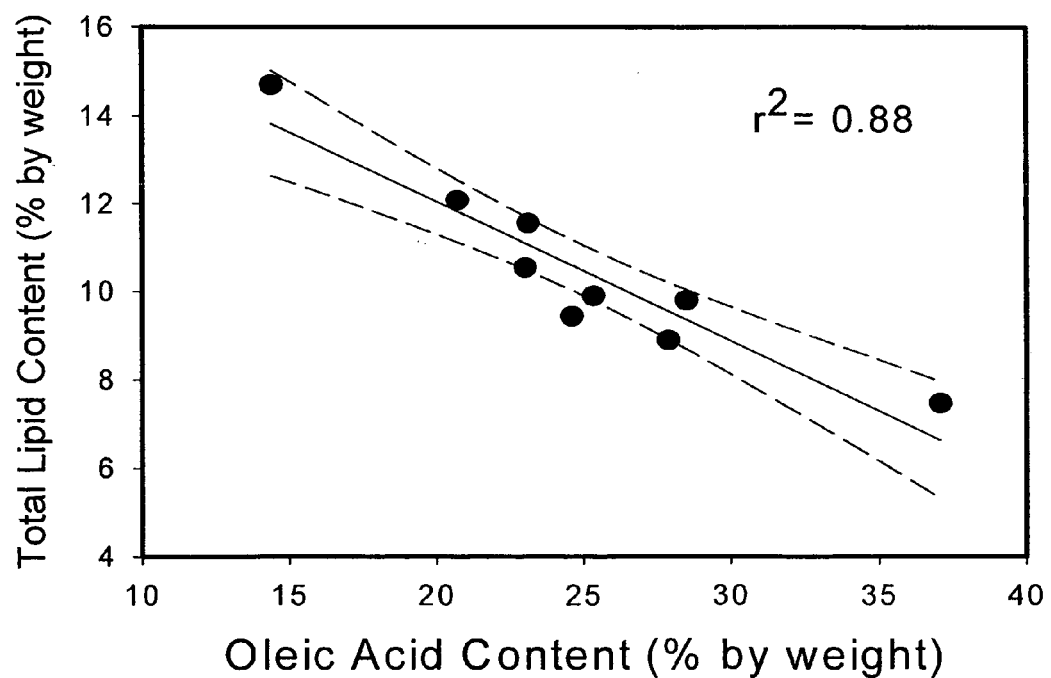
FIG. 5 provides correlation results for total lipid content and oleic acid content (% by weight) in transformed seed. Seeds were selfed progeny from primary transformants (T0 individuals).
Figure 6:
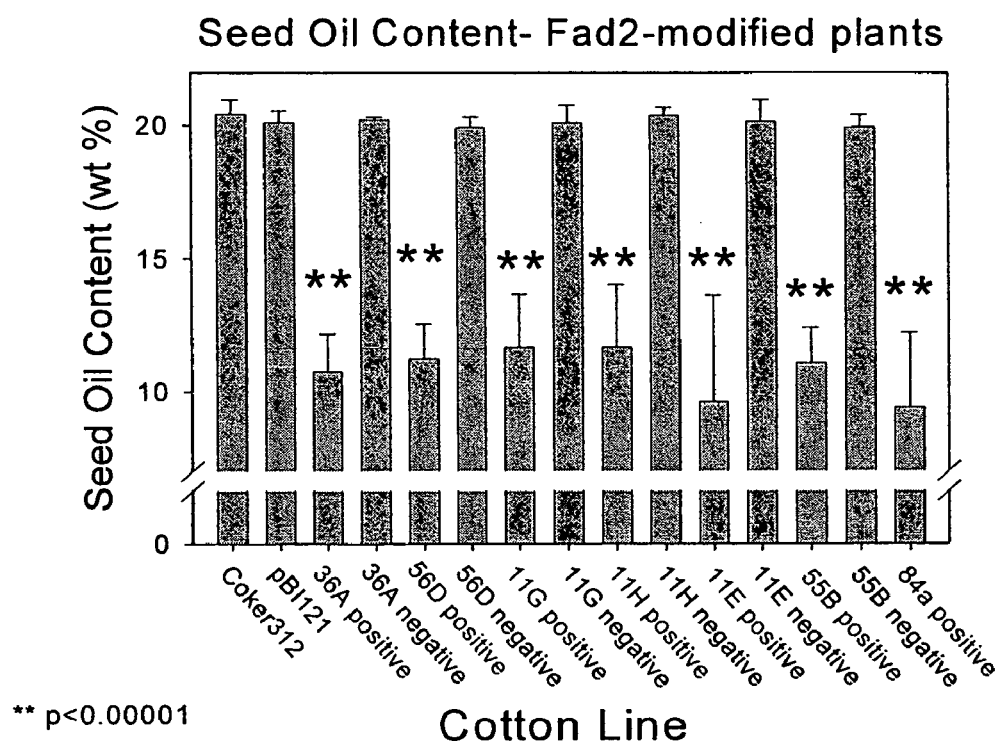
FIG. 6 provides mean seed oil content (% by weight) for transgenic FAD2 expressing and non-expressing plants. Seeds were selfed progeny from T1 individuals.

T1 seed from eight independent insertion events of the FAD2 gene were analyzed for total lipid using an ether extraction method and for oleic acid percent. For total lipid extraction, three subsamples, consisting of 3 or 4 seeds each, were analyzed. The means of results for the subsamples are given in FIG. 5. Oil percent and oleic acid percent in these T1 cotton seeds are highly correlated ($r^2$=0.88), suggesting that the FAD2 gene, acting as a dominant negative allele, interferes with at least two endoplasmic reticulum-located lipid biosynthesis processes, fatty acid desaturation and lipid accumulation.

Example 2

Oleic Acid and Total Lipid Content in Seeds From a Primary Transformant Cotton Line Seeds from line ZpH 84a primary transformants and several T3 progeny derived from this line were compared with respect to the relationship between oleic acid percentage and total lipid content. See Table I, below. Oleic acid percentage was measured by gas chromatography on lipid extracted from 8-seed pooled samples. Total lipid was measured gravimetrically on extracts from 3- to 4-seed pooled samples (approximately 250 mg mass). Total lipid values are mean±standard deviation, n=3. Values for seeds of the Coker312 background line (and vector-only control, PBI-121) are shown for comparison. These data indicate that a reduction in seed oil was associated with a modification in oleic acid percentage, although values varied somewhat.

TABLE I

Oleic Acid and Total Lipid Content in Transformed Cotton Seed

| Seed | % Oleic acid | % Total lipid |
|---|---|---|
| Coker312 | 14.7 | 14.4 ± 1.13 |
| PBI-121 | 17.4 | 17.6 ± 1.47 |
| Zph 84a T1 (primary transgenic parent) | 28.5 | 9.78 ± 3.21 |
| Zph 84a T3-1 (7' = 7221 T2 parent) | 24.3 | 4.08 ± 0.28 |
| Zph 84a T3-2 (10' = 10221 T2 parent) | 32.6 | 5.86 ± 0.67 |
| Zph 84a T3-3 (10' = 10412 T2 parent) | 20.3 | 7.01 ± 0.45 |

Example 3

Seed Germination of Transgenic Plants

T1 seed from the eight independent insertion events discussed in Example 1 were germinated using methods known in the art specifically to maximize percent germination. Briefly, the conditions included germination in moist blotter paper maintained at a constant temperature of 30° C. Because the seeds had been stored for 4 years prior to germination, which exceeds the optimum storage life for cotton planting seed of 2 to 3 years, germination was conducted under optimum temperatures for cotton as defined by the International Seed Testing Association (30° C.) and near-sterile conditions. Those seedlings that successfully germinated were evaluated for hypocotyl and radicle length on day 4 after planting, prior to transplanting into potting soil. None of the seedlings of the lowest oil content insertion event survived.

When plants reached the 10-leaf stage, PCR was used to determine the presence of the canola FAD2 gene insert in leaf tissue. The methods of Chapman et al., *J. Am. Oil Chem. Soc.* 78:941-947, 2001 were used to confirm the insertion of the foreign canola FAD2 gene into cotton plant cells. Briefly, this method consists of leaf tissue collection and preservation at −20° C., followed by extraction of DNA and PCR amplification using end point PCR and primer sequences unique to the canola FAD2 gene sequence.

Cotton DNA was used as template for PCR analysis with two canola-specific fad2 primers (forward: 5'-ATGCAAGT-GTCTCCTCCCTCC-3' (SEQ ID NO:1) and reverse: 5'-CGTTAACATCACGGTCGCTC-3' (SEQ ID NO:2)). These primers specifically amplified a 528 bp fragment of the canola fad2. The PCR reaction mixtures contained approximately 1 μg of template DNA, 1 μM of each primer, 0.2 mM dNTPs and 1.25 units of AmpliTaq™ DNA polymerase. Reaction conditions were 32 cycles of 95° C. (45 seconds), 60° C. (45 seconds) and 72° C. (2 minutes). The PCR amplification products were evaluated by agarose gel electrophoresis. Plants PCR-positive for the presence of the canola FAD2 gene had reduced radicle and hypocotyl length, supporting the hypothesis that low-oil content seeds can experience a reduced rate of seedling development relative to high-oil content seeds. See Table II, below.

TABLE II

Radicle and Hypocotyl Length

| Canola FAD2 Gene Present by PCR? | Radicle Length (cm) | Hypocotyl Length (cm) |
|---|---|---|
| yes | 5.05 | 6.21 |
| no | 6.89 | 7.65 |

A second planting was initiated in May 2005 following the above protocol using seed from T1 plants grown in 2004. This recently harvested seed had been assessed for seed oil content using nuclear magnetic resonance according to standard methods. Table III below provides data showing the relationship between seed oil content, germination and seedling growth.

TABLE III

Table III. Summary of seed oil content, percent germination, and 5-day-old seedling growth characteristics for selected transgenic lines (T2) compared with controls (Coker 312 untransformed, pBI121 vector control, and null segregants (N)).

| Parental line | Seed oil content (wt %) | Germination at 5 days (%) | Hypocotyl length (mm) | Radicle length (mm) | Total length (mm) |
|---|---|---|---|---|---|
| Coker 312-2 | 20.91 | 100 | 88.7 ± 13.0$^a$ | 83.0 ± 23.1 | 170.7 ± 31.6 |
| PBI121-15 | 20.63 | 100 | 63.0 ± 34.1 | 111.5 ± 26.4 | 174.5 ± 47.2 |
| ZPH55B-3 (T) | 9.18 | 40 | 65.6 ± 36.4 (NS) | 84.1 ± 51.4 (NS) | 149.7 ± 74.6 (NS) |
| ZPH55B-12 (T) | 10.23 | 55 | 74.1 ± 41.6 (NS) | 79.2 ± 49.2 (NS) | 144.2 ± 77.7 (NS) |
| ZPH55B-10 (T) | 10.11 | 35 | 45.7 ± 29.3** | 41.8 ± 30.3** | 87.6 ± 55.6** |
| ZPH55B-8 (N) | 20.46 | 85 | 81.5 ± 25.0 | 95.5 ± 37.1 | 177.3 ± 56.8 |
| ZPH36A-13 (T) | 8.79 | 55 | 56.8 ± 37.6 (NS) | 68.0 ± 43.6 (NS) | 124.8 ± 78.7 (NS) |
| ZPH36A-9 (N) | 7.96 | 50 | 35.9 ± 30.9** | 41.0 ± 31.0** | 76.9 ± 59.4** |
| ZPH36A-1 (N) | 20.33 | 100 | 65.3 ± 22.5 | 91.0 C 36.8 | 156.4 ± 52.6 |
| ZPH11G-13 (T) | 8.77 | 45 | 51.5 ± 27.5* | 49.5 ± 30.5**** | 101.0 ± 43.1**** |
| ZPH11G-5 (T) | 9.62 | 25 | 53.0 ± 34.7** | 38.4 ± 22.2**** | 91.4 ± 56.3**** |
| ZPH11G-8 (N) | 20.67 | 95 | 80.7 ± 16.4 | 95.6 ± 11.3 | 171.0 ± 22.4 |
| ZPH11E-11 (T) | 8.89 | 20 | 39.0 ± 8.72**** | 32.0 ± 4.54***** | 71.0 6.06***** |
| ZPH11E-8 (T) | 2.14 | 0 | N/A | N/A | N/A |
| ZPH11E-6 (T) | 20.29 | 90 | 89.8 C 18.5 | 114.7 C 23.2 | 204.5 C 31.5 |

$^a$mean and standard deviation, n = 4-20;
*p < 0.05, t-test vs null;
**p < 0.005, t-test vs null;
***p < 0.0005, t-test vs null;
****p < 0.00005, t-test vs null
*****p < 0.000005, t-test vs null;
(NS) p > 0.1, t-test vs null.
N/A, not applicable.

Example 4

Expression of the Transgene in Seed Does Not Impact Growth Through the First Bloom Developmental Phase Total nodes and plant height, in centimeters from the cotyledons, were measured during the 43 days after planting. Representative data are reported in Table IV, below. The set of plants PCR-positive for the canola FAD2 gene had fewer nodes and reduced plant height compared with the near isogenic PCR-negative plants at 22 days after planting. By 28 days after planting, however, the differences observed at 4 and 22 days were no longer evident, and both populations of plants appeared to be growing normally. Expressing the FAD2 gene using a seed-specific promoter, therefore, resulted in delayed germination without a durable impact on seedling growth.

TABLE IV

Effect of Presence of Transgene on Total Nodes and Plant Height

| Days After Planting | Total Nodes (Canola FAD2 Gene Present/Absent by PCR) | Plant Height (Canola FAD2 Gene Present/Absent by PCR) |
|---|---|---|
| 22 | 2.99/3.77 | 6.29/5.95 |
| 28 | 3.70/4.08 | 10.35/10.35 |
| 36 | 5.56/5.33 | 14.83/15.76 |
| 43 | 9.93/10.37 | 32.31/31.84 |
| 59 | 12.93/13.21 | 62.24/62.80 |

Example 5

Expression of the Transgene in Seed Impacts Seed and Fiber Constituents

Individual plants expressing the FAD2 transgene and non-expressing controls (non-expressing transgene, azygous plant or non-transformed Coker 312 plants) were harvested to determine the fiber and seed yields along with various seed parameters. Bolls were harvested from all T1 plants and each position was noted. Total seed cotton weight was measured for each boll and recorded by node position. Samples were grouped into two zones, one in the central region of the plant (nodes 6, 7 and 8) and one zone encompassing remaining nodes above and below the central zone (vegetative and lower nodes and those above position 8). Samples for each zone were pooled and ginned in a benchtop 10-saw cotton gin, and fiber and seed weights recorded for each zone for each plant. Seed index (weight of 100 seeds) also was recorded for each zone, and the total number of seeds and bolls from each zone were tabulated. Fifteen-seed samples from zone one of each plant were placed into glass vials and sterilized by autoclaving. Oil content (by weight %) was measured in each 15-seed sample by low-frequency pulsed-field $^1$H-NMR in a benchtop minispec (Bruker Instruments™).

Figure 7:
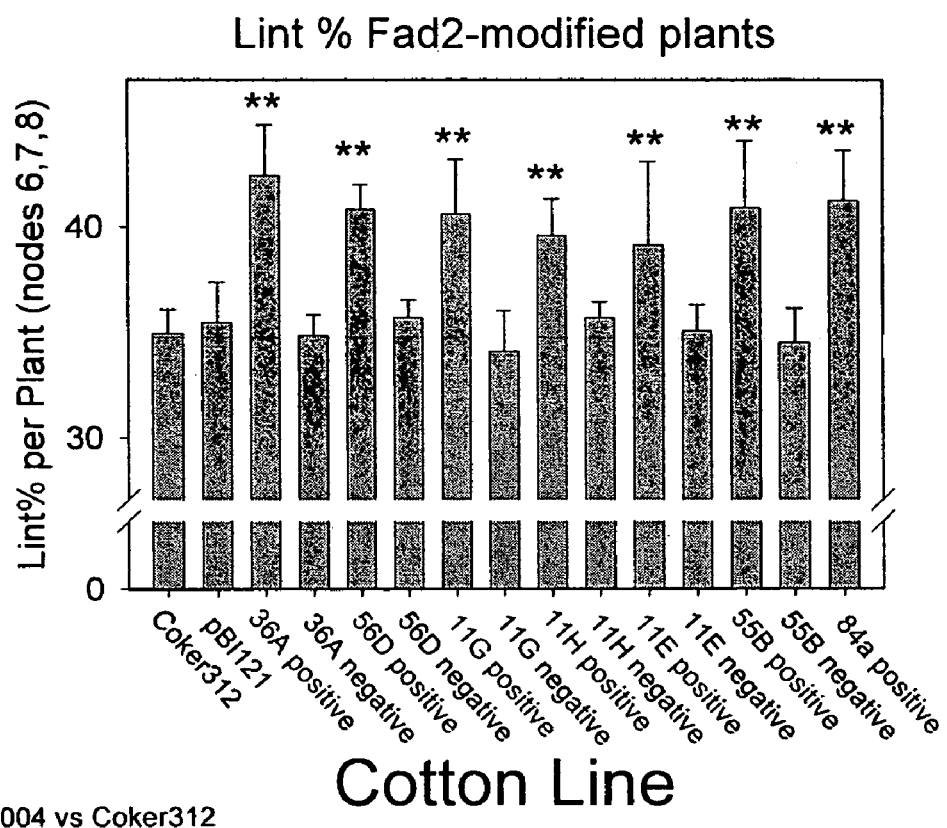
FIG. 7 provides mean seed lint percent (100×grams lint/ grams lint+grams seed)) for transgenic FAD2 expressing and non-expressing plants. Seeds were selfed progeny from T1 individuals.
Figure 8:
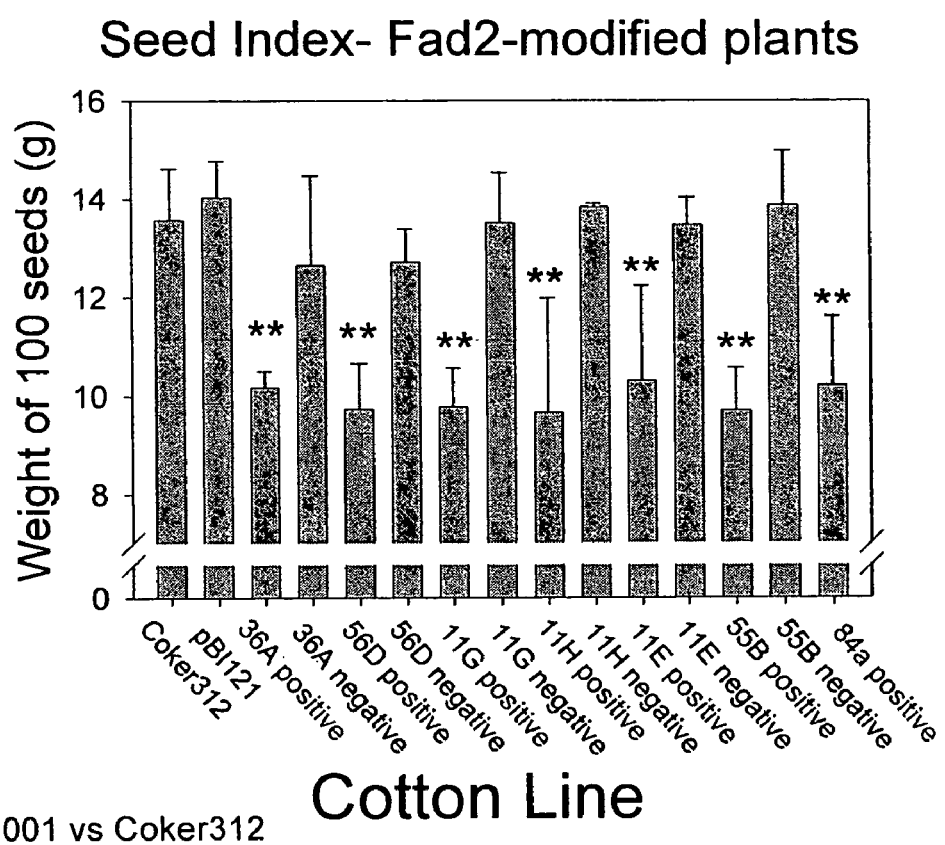
FIG. 8 provides mean seed index (grams per 100 delinted seeds) for transgenic FAD2 expressing and non-expressing plants. Seeds were selfed progeny from T1 individuals.
Figure 9:
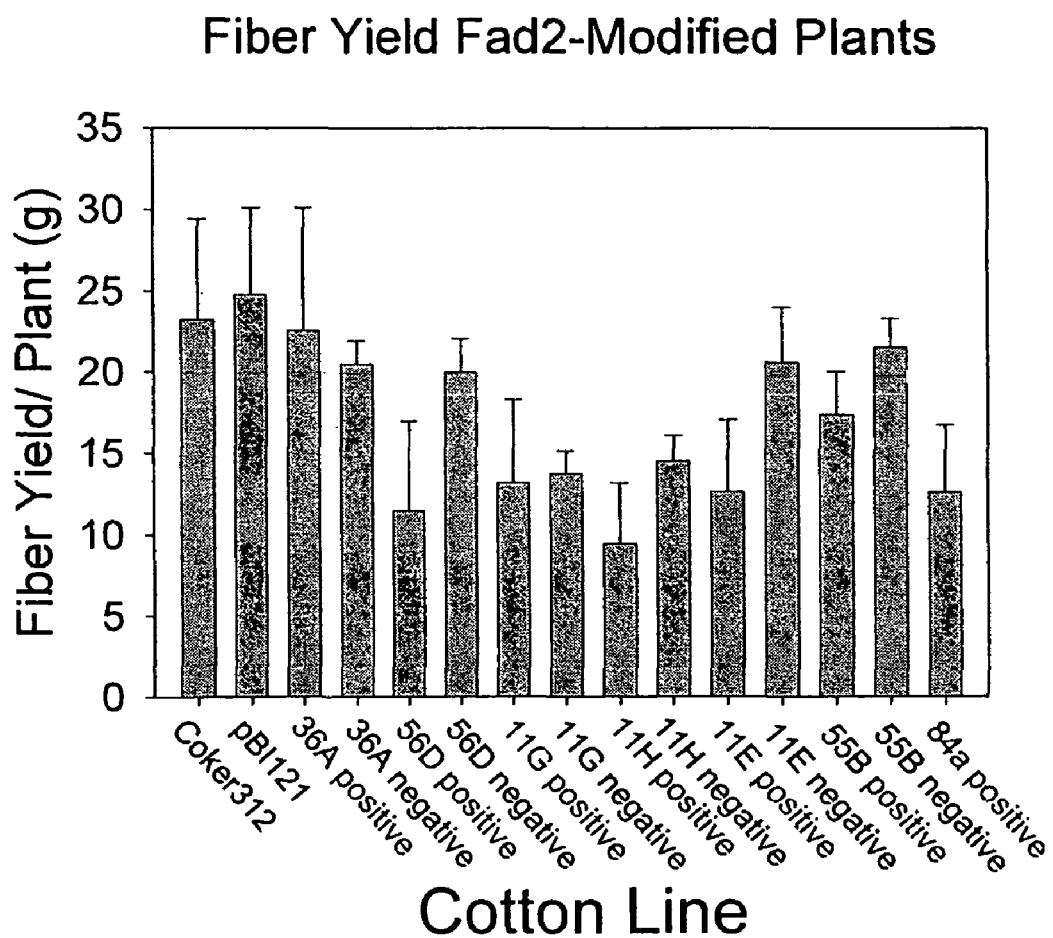
FIG. 9 provides mean fiber yield (grams per plant) for transgenic FAD2 expressing and non-expressing plants. Seeds were selfed progeny from T1 individuals.
Figure 10:
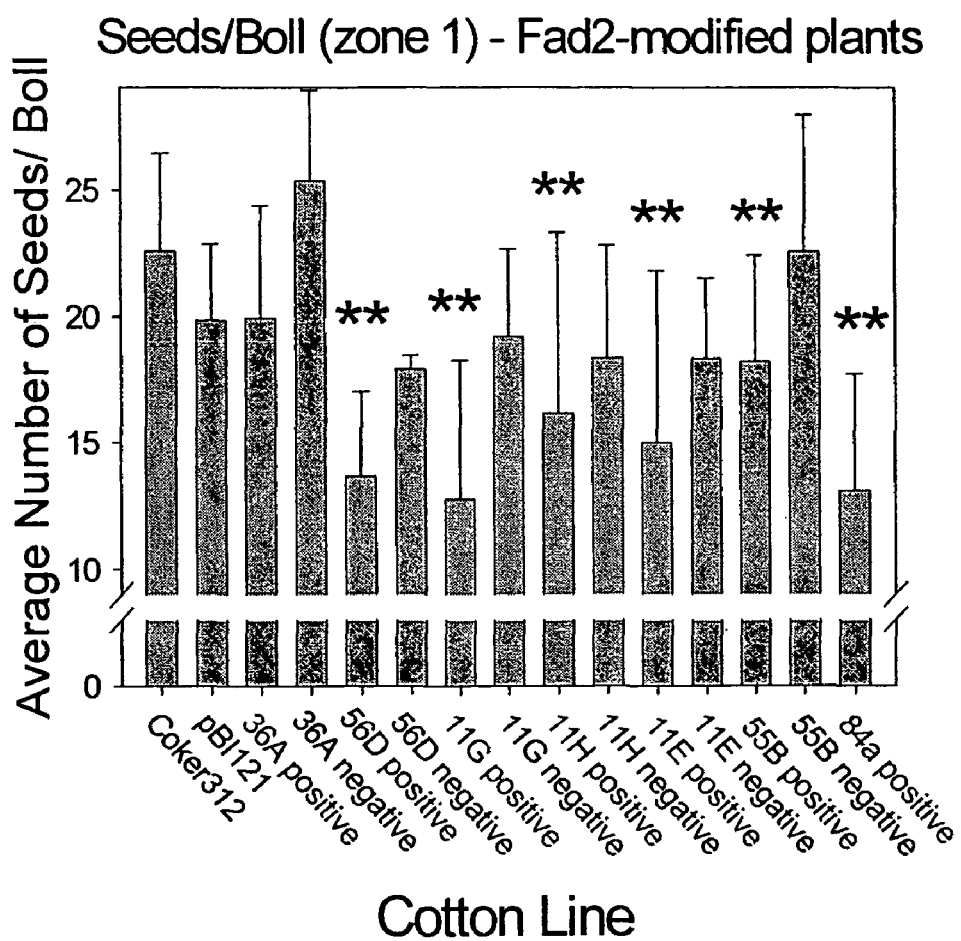
FIG. 10 provides average number of seeds/boll for FAD2- modified plants. Seeds were selfed progeny from T1 individuals.

FIGS. 6-9 show the relationship between FAD2 expression and seed oil content (FIG. 6), lint percent in the central zone of the plant (nodes 6, 7 and 8; FIG. 7), seed index (FIG. 8), fiber yield per plant (FIG. 9) and number of seeds per boll (FIG. 10). FAD2 expression had a highly significant impact on the first three parameters, indicating that the dominant negative allele methods are able to alter oil content. Fiber yield was not consistently increased in FAD2-expressing plants due to low seed set (FIG. 9). In the confines of an insect-controlled glasshouse, cross pollination by insects is restricted. Thus self-pollination predominates.

The phaseolin promoter has been shown to express in the seed and anthers of multiple plant species (*Nicotiana tabacum, Phaseolus vulgaris, Vicia faba* and *Arabidopsis thaliana*). See Chandrasekharan et al., *Plant J.* 33:853-866, 2003; Zakraov et al., *J. Exp. Botany* 55(402):1463-1471, 2004. Transgene expression also has been shown to result in pollen sterility for xylanase pollen expression and for Diphtheria Toxin A pollen expression. See Zakharov et al., *J. Exp. Botany* 55(402):1463-1471, 2004; van der Geest et al., *Plant*

Physiol. 109:1151-1158, 1995. Due to the role of stored triacylglycerol lipids in anthers, it is not unexpected that anther expression of oil-suppression transgenes also should reduce pollen function and seed set. Thus, if reduced seed set is to be avoided with oil-suppression technology, the use of promoters with limited to negligible expression in pollen, such as AGP, are most preferred.

Example 6

Field Emergence and Seedling Vigor of Cotton Planting Seed Lots with Varying Oil Content To confirm the relationship between seed oil content and resulting seedling development, forty commercial lots of a low-oil content variety cotton, DP555 BGRR, were analyzed using the methods described in Example 2 for oil content. Samples also were planted in a four-replication trial (Winterville, Miss., into warm soils on May 26 to a depth of approximately 2 inches from the surface. Normal planting depth is no more than 1 inches deep at this location, thus a 2-inch deep planting created emergence stress on the seedlings, thereby causing longer hypocotyls since they emerge from the greater depth. These forty seed lots were assessed for warm germination (20° C. for 16 hours alternating with 30° C. for 8 hours) and cool germination (constant 18° C.) using industry standard methods. Simple correlations were developed for the following parameters: oil content (after warm germination and cool germination), final percent stand survival at day 28, and seedling vigor rating at day 8 post planting, Table V. The standard deviation of seed oil content of one of the lots was twice that of the next most variable lot. This lot was excluded from the analysis, leaving a total of 39 lots.

TABLE V

Simple Correlation Coefficients Between Seed Oil Content and Various Seed Quality Parameters

|  | Vigor DAP8 | Survival DAP19 | Year Grown | Warm Germinat. (%) | Cool Germinat. (%) | Seed Weight (g/100 seeds) |
| --- | --- | --- | --- | --- | --- | --- |
| Oil % | −0.458 | 0.440 | −0.102 | −0.203 | 0.202 | 0.255 |
| Seed Weight | −0.352 | 0.157 | −0.172 | 0.022 | 0.278 | — |
| Cool Germinat. | −0.229 | 0.120 | 0.059 | 0.501 | — | — |
| Warm Germinat. | −0.209 | 0.398 | 0.000 | — | — | — |
| Year | −0.073 | 0.052 | — | — | — | — |
| Survival | −0.834 | — | — | — | — | — |

Vigor Rating (a visual rating with 1 being best, and 5 being worst) has been developed as a predictor of seedling survival. Seedlings with high vigor have an increased chance of surviving. The highly significant correlation between vigor and survival (r=−0.834; N=39; P=<0.01) provides an internal check on the field protocol and data collection. Following this anticipated correlation, the next best predictor of both vigor and survival was seed oil percent. Seed oil percent was a superior predictor of field performance than either warm germination or cool germination. These data indicate that reduced oil content of cotton seeds impairs their normal germination in the field.

Example 7

Transgenic Cotton Seeds with Disrupted Seed-Storage Embryo Tissue

Figure 3:
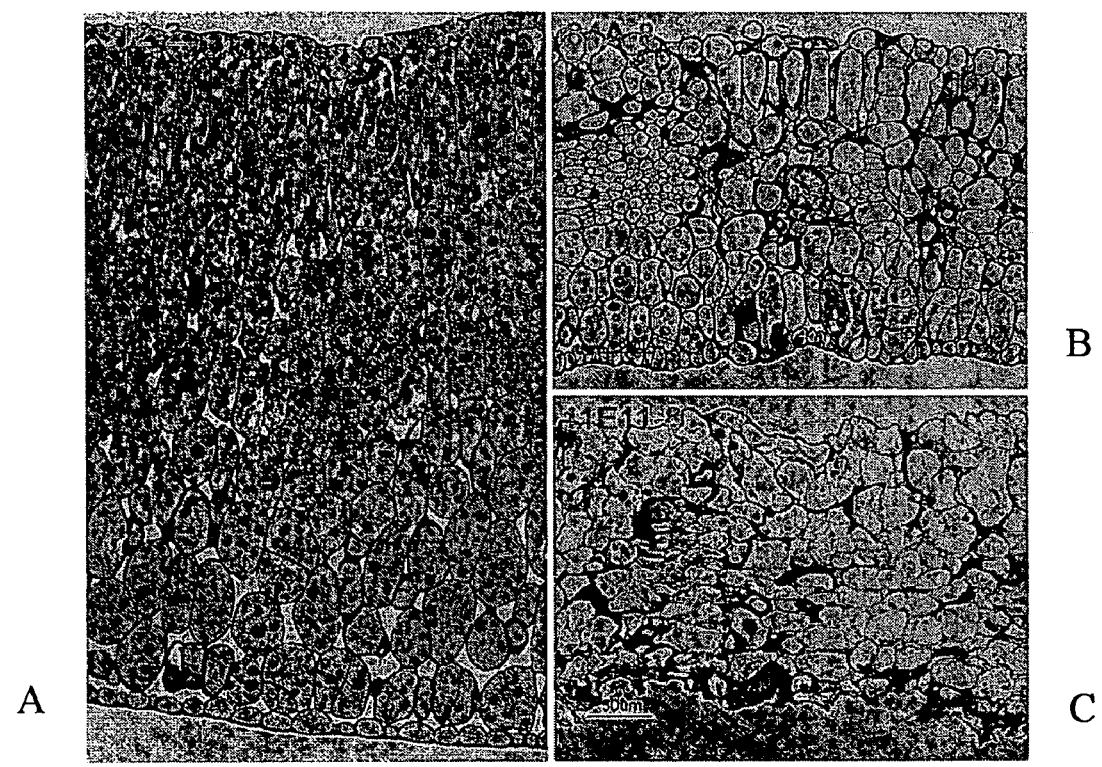
FIG. 3 is a micrograph of cross sections of cotyledon from (A) high oil (21% w/w) and (B and C) low oil (4% and 2% w/w) seeds stained and visualized by conventional brightfield microscopy.
Figure 4:
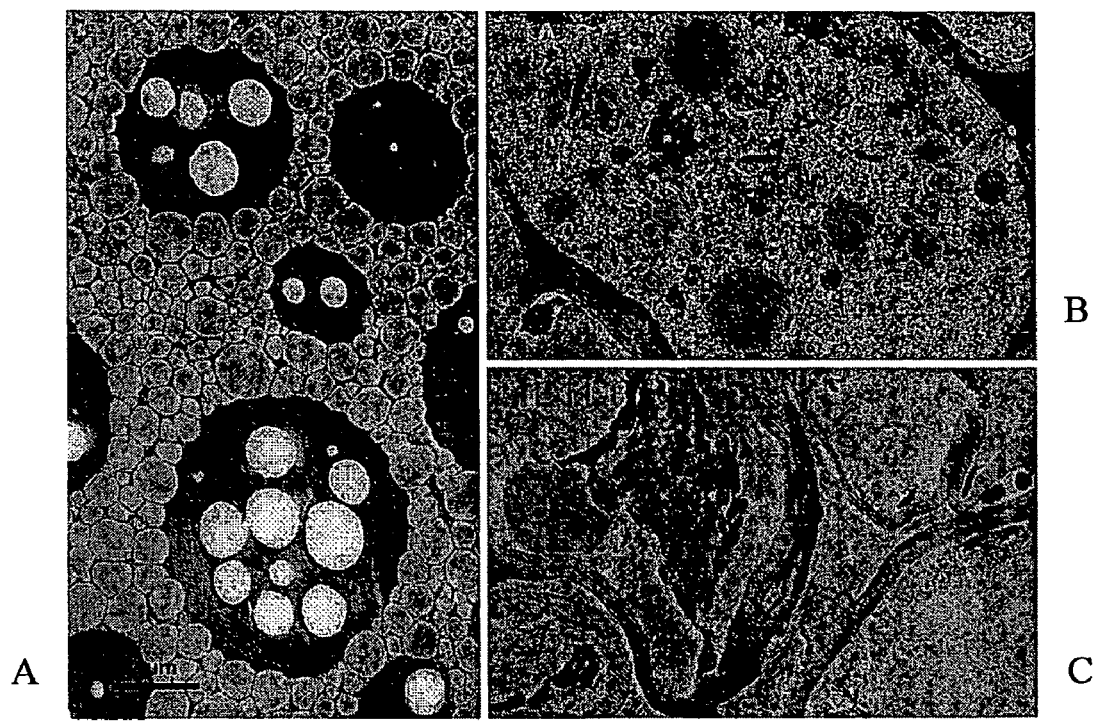
FIG. 4 is a micrograph of cross sections of cotyledon from (A) high oil (21% w/w) and (B and C) low oil (4% and 2% w/w) seeds stained and visualized by conventional transmission electron microscopy.

FIGS. 3 and 4 show light and electron microscope micrographs for seed cotyledons from 3 plants, a high seed oil line (Coker 312), a medium seed oil line (Zph84A-8) and a low seed oil line (Zph11E-8). Both the medium and low seed oil lines express the FAD2 Dominant Negative Mutation and show a disruption to both oil and protein bodies in the cotyledonary mesophyll, as compared with the Coker 312 tissue. Since protein bodies and oil bodies are assembled in the endoplasmic reticulum, which is also the site of FAD2 enzyme function, cotyledonary tissue expressing a Dominant Negative Mutant FAD2 allele has impaired development of both protein and oil bodies. These micrographs show the functioning of the FAD2 gene in cotyledonary tissue.

Example 8

Transgenic Cotton Seeds with Reduced Nutrient Extraction

Seed cotton from 106 individual T1 plants, PCR-negative and PCR-positive for the presence of the mutant canola FAD2 gene, were hand harvested. These bolls were ginned separately to allow determination of fiber weight per boll, seed weight per boll and seed number per boll. From these determinations a calculation of fiber weight per seed was derived. Aliquots of 10 seeds each were weighed and devitalized by autoclaving (120° C., 20 min). Oil content was determined by nuclear magnetic resonance (NMR) according to the International Organization for Standardization, reference number ISO 10565:1992(E) Oilseeds-Simultaneous determination of oil and moisture contents-Method using pulsed nuclear magnetic resonance spectroscopy. A Bruker NMS 110 Minispec NMR Analyzer calibrated with cottonseed oil was used to estimate percent oil by seed weight (Rutar, (1989) J Agric Food Chem 37: 67-70).

After the non-destructive determination of oil content, these seeds were analyzed for moisture content, total N, total P and total K at a commercial plant testing facility with the following methods (moisture content by AOAC 4.1.06 from the Official Methods of Analysis of AOAC International, 16th Edition, 1995; total N by AOAC 4.2.08 from the Official Methods of Analysis of AOAC International, 17th Edition, 1998; and total P and K by SW-6010B from the USEPA, SW-846, Test Methods for Evaluating Solid Wastes, Physical/Chemical Methods, 3rd Ed. Current Revision). The following results were obtained (Table VI and Table VII.)

TABLE VI

Average Seed Index, Seed Oil Percent and Fiber per Seed in T2 Fuzzy Cotton Seed of Transgenic Events Expressing or Non-Expressing a Mutant Canola FAD2 Protein.

| Cotton Line | FAD2 PCR | Seed Index (g/100 fuzzy seeds) | Seed Oil % | Fiber (mg/seed) |
| --- | --- | --- | --- | --- |
| Coker312 | negative | 13.66 | 20.4 | 75.1 |
| PBI121 | negative | 14.16 | 20.1 | 78.7 |
| Zph56D | negative | 12.61 | 19.9 | 73.6 |
| Zph55B | negative | 11.55 | 17.8 | 65.8 |
| Zph11G | negative | 13.67 | 20.1 | 71.9 |
| Zph11H | negative | 14.04 | 20.4 | 77.2 |
| Zph11E | negative | 13.56 | 20.1 | 74.3 |
| Zph36A | negative | 12.61 | 20.2 | 69.8 |
| average |  | 13.23 | 19.9 | 73.3 |

TABLE VI-continued

Average Seed Index, Seed Oil Percent and Fiber per Seed in T2 Fuzzy Cotton Seed of Transgenic Events Expressing or Non-Expressing a Mutant Canola FAD2 Protein.

| Cotton Line | FAD2 PCR | Seed Index (g/100 fuzzy seeds) | Seed Oil % | Fiber (mg/seed) |
|---|---|---|---|---|
| Zph55B | positive | 9.36 | 10.5 | 66.3 |
| Zph56D | positive | 10.14 | 11.2 | 69.4 |
| Zph11G | positive | 8.97 | 11.7 | 70.5 |
| Zph11H | positive | 9.13 | 11.7 | 64.2 |
| Zph11E | positive | 9.34 | 9.6 | 67.1 |
| Zph36A | positive | 9.58 | 10.8 | 78.4 |
| Zph84A | positive | 9.56 | 9.4 | 74.1 |
| average | | 9.44 | 10.7 | 70.0 |

TABLE VII

Table VII. Average Nitrogen, Potassium and Phosphate Content as Reported in Weight per Weight of Seed and Weight per Weight of Fiber in T2 Fuzzy Cotton Seed of Transgenic Events Expressing or Non-Expressing a Mutant Canola FAD2 Protein. One bale of fiber weighs 480 pounds.

| D&PL lot # | FAD2 PCR | N % | K (mg/Kg) | P (mg/Kg) | N (lbs/bale) | K2O (lbs/bale) | P2O5 (lbs/bale) |
|---|---|---|---|---|---|---|---|
| Coker312 | negative | 4.23 | 12,806 | 10,409 | 37.2 | 13.5 | 21.1 |
| PBI121 | negative | 4.60 | 12,752 | 10,237 | 39.7 | 13.2 | 20.3 |
| ZpH56D | negative | 4.83 | 15,465 | 11,954 | 39.9 | 15.5 | 23.0 |
| ZpH55B | negative | 4.53 | 17,039 | 13,668 | 38.2 | 17.2 | 26.5 |
| Zph11G | negative | 4.59 | 14,652 | 9,022 | 41.8 | 16.1 | 19.0 |
| ZpH11H | negative | 4.89 | 9,822 | 6,669 | 42.6 | 10.3 | 13.4 |
| Zph11E | negative | 4.63 | 15,381 | 9,172 | 40.6 | 16.2 | 18.5 |
| ZpH36A | negative | 6.41 | 15,841 | 9,453 | 53.6 | 16.5 | 18.9 |
| average | | 4.84 | 14,220 | 10,073 | 41.7 | 14.8 | 20.1 |
| ZpH55B | positive | 4.34 | 11,862 | 7,638 | 31.4 | 9.6 | 11.9 |
| ZpH56D | positive | 4.82 | 13,116 | 9,084 | 33.9 | 11.2 | 15.0 |
| Zph11G | positive | 4.11 | 12,243 | 6,439 | 25.8 | 9.0 | 9.0 |
| ZpH11H | positive | 4.18 | 12,448 | 6,832 | 28.6 | 10.2 | 10.7 |
| ZpH11E | positive | 5.01 | 12,228 | 6,702 | 32.6 | 9.8 | 10.3 |
| ZpH36A | positive | 4.02 | 13,609 | 6,884 | 23.6 | 9.6 | 9.3 |
| ZpH84A | positive | 4.14 | 12,705 | 7,216 | 25.9 | 9.6 | 10.4 |
| average | | 4.37 | 12,602 | 7,256 | 28.8 | 9.9 | 10.9 |

Figure 11:
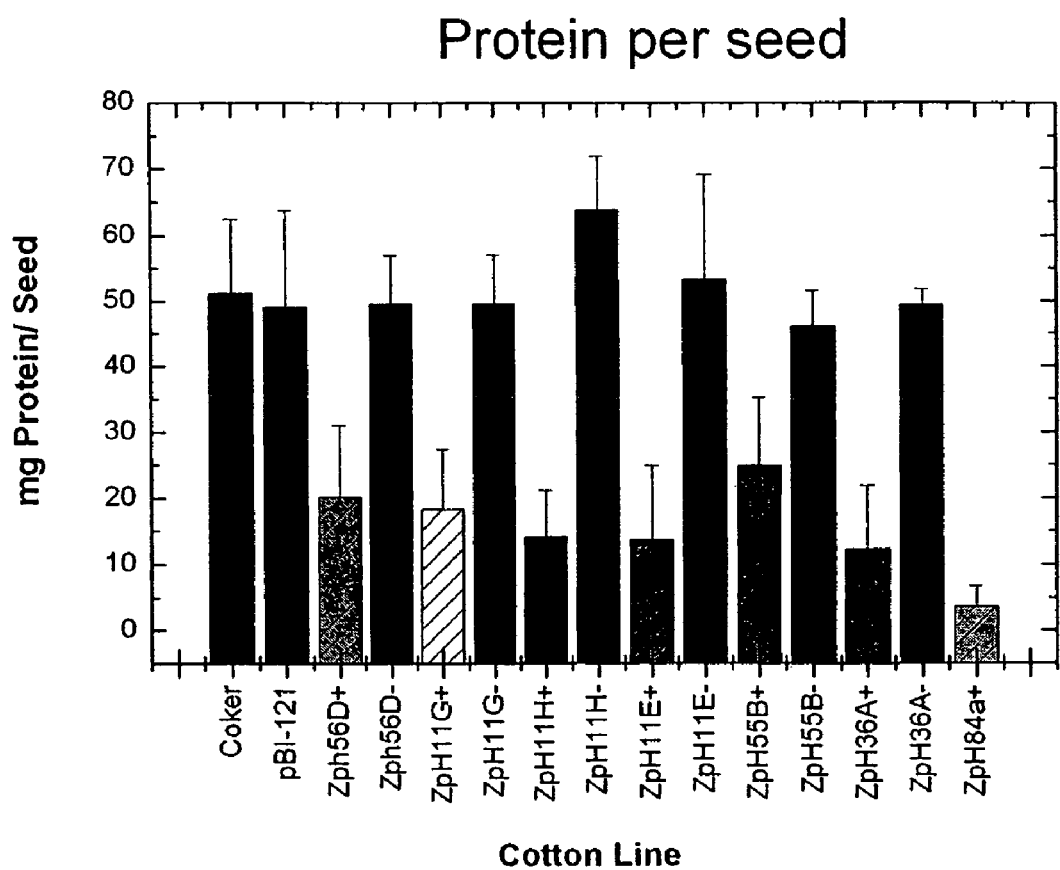
FIG. 11 provides total seed protein per seed harvested from FAD2 PCR positive and PCR negative T1 plants.

Ten-seed pooled samples were de-husked, flash-frozen in liquid nitrogen and embryos were crushed in a chilled mortar. Crushed seed samples were then homogenized in a glass vessel with a motorized pestle in extraction buffer (0.5M Tris, pH 8.65, 50 mM EDTA, 100 mM KCl, 2% beta-mercaptoethanol) and Tris buffer-saturated phenol following the procedure of Ferguson et al., 1996 [Ferguson, D L, Turley, R B, and Meredith W R, Jr., 1996, J. Agric. Food Chem. 44: 4022-4029]. Homogenates were centrifuged at 13,000×g for 15 min, and the phenol layer was collected and washed two times with equal volumes of extraction buffer. Total protein was estimated from diluted aliquots of the phenol extracts according to Bradford (1976) [Bradford M M, 1976, Anal. Biochem. 12: 248-254] See FIG. 11.

Figure 15:
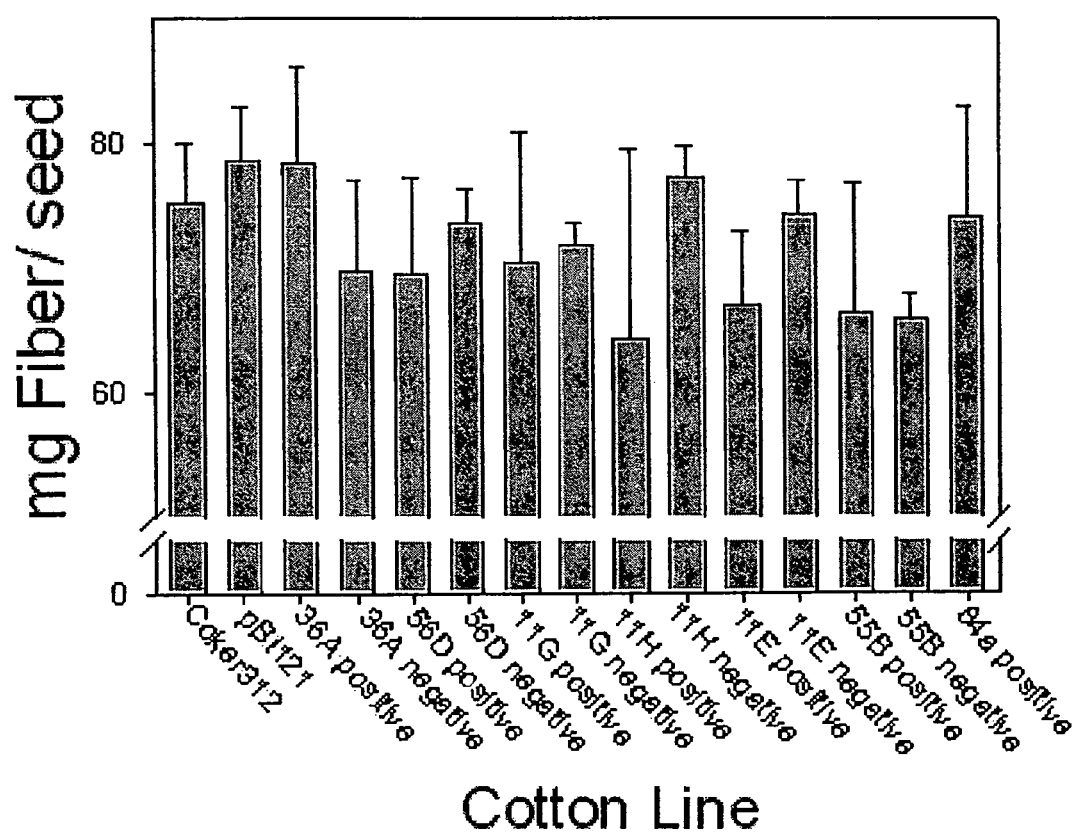
FIG. 15 provides total lint fiber mass per seed harvested from FAD2 PCR positive and PCR negative transgenic T1 plants.

Fuzzy cotton seed harboring a nonfunctional canola FAD2 allele (FAD2 positive), relative to the FAD2 negative seed (null segregants), had consistently lower protein, nitrogen, phosphorus and potassium content per mass of fiber for all transgenic events tested, see Tables 6 and 7 and FIGS. 11, 12, 13 and 14. Protein was reduced to a greater degree than N, P or K in the seed providing further support to the claim that the FAD2 Dominant Negative Mutation is disruption protein bodies in cotton seeds. Considering that there were no significant differences in fibers per seed between FAD2 positive and negative seeds, as seen in FIG. 15, the reduction in seed nutrients allows a substantial savings in soil nutrients for comparable fiber yields.

In both hand and machine picked cotton production systems only the seed cotton (seed with fiber attached) are removed from the field. Thus, these results clearly demonstrate the utility of embodiments of the disclosed inventions in reducing the fertilizer requirement to produce cotton fiber. In high input cotton production, fertilizer cost and early season insect pest feeding may be substantially reduced with plants made by the disclosed methods. In low input cotton, less nutrient extraction from the soil enhances the long term sustainability of agriculture while increasing fiber yield.

When the seed nutrient contents were correlated against other seed parameters the following table of correlation coefficients was determined.

TABLE VIII

Cross Correlations between Parameters of Seed Harvested from Individual FAD2 Positive or Negative Plants. Cross Correlations N = 106 P.01 = 0.254

| | Seed index (g/100) | Seed Oil | Fiber | N/Fiber | K/Fiber |
|---|---|---|---|---|---|
| P (g/g fiber) | 0.658 | 0.616 | 0.039 | 0.622 | 0.908 |
| K (g/g fiber) | 0.556 | 0.515 | −0.075 | 0.624 | |
| N (g/g fiber) | 0.584 | 0.563 | −0.223 | | |
| fiber (g/seed) | 0.330 | 0.292 | | | |
| oil % (w/w) | 0.860 | | | | |

All correlations reported in Table VIII are statistically significant at the 1% level with the exception of correlations between nutrients and fiber mass per seed. Since fiber mass accumulates in a boll approximately 15 days in advance of the embryo mass, the reductions in embryo N, P and K resulted in only slight impact on fiber development. This is further evidence for the value of embodiments of this invention, as a savings in N, P and K fertilizer that can be realized without interfering with fiber development, a biological process that has been optimized for spinning performance by plant breeders (both modern and primitive) for over 5,000 years.

Correlations among the embryo parameters (oil, N, P and K) were all highly significant, as expected from the effective functioning of the FAD2 Dominant Negative Mutation on the endoplasmic reticulum located oil and protein body formation. Since potassium is the dominant cation bound to phytate (the storage form of phosphorus in protein bodies) a reduction in phytate is anticipated to have a concomitant reduction in potassium. Among the embryo parameters, the highest correlations are between P and K (r=0.908), with less significant correlations between P and N (r=0.662) and between K and N (r=0.624) substantiating the close phytate-potassium relationship in protein bodies.

Example 9

Transgenic Cotton Plants with Enhanced Fiber Yield

Seed harvested from T1 plants of four independent FAD2 events, both PCR positive plants and PCR negative null segregant plants, were germinated, tested for the presence of the FAD2 gene and then grown to maturity in a glasshouse under uniform environmental and production practices. The following table lists the yield components for 12 T2 FAD2 PCR negative plants and 10 T2 FAD2 PCR positive plants.

TABLE IX

Seed and Fiber Yield Components for Glasshouse Grown T2 FAD2 Positive Plants Expressed as a Percent of the T2 FAD2 Negative Plants Seed Oil Percent - 45%
Seeds per Bolls - 108%
Number of Bolls per Plant - 99%
Total Boll Weight per Plant - 101%
Total Seed Weight per Plant - 88%
Seed Index (g/100 seeds) - 78%
Lint Index (g/100 seeds) - 115%
Lint Percent - 125%
Lint Weight per Plant - 123%

Although the harvested mass per plant (Total Boll Weight and Number of Bolls per Plant) were similar for FAD2 positive and negative plants, the substantial reduction in seed oil and seed index in the FAD2 positive plants was matched with a substantial increase in Lint Percent and Lint Weight in these same plants, relative to the PCR negative plants. FAD2 positive plants had reduced seed yield and increased fiber yield, relative to FAD2 negative plants, providing support for the yield enhancement benefits derived from this invention.

Example 10

Figure 16:
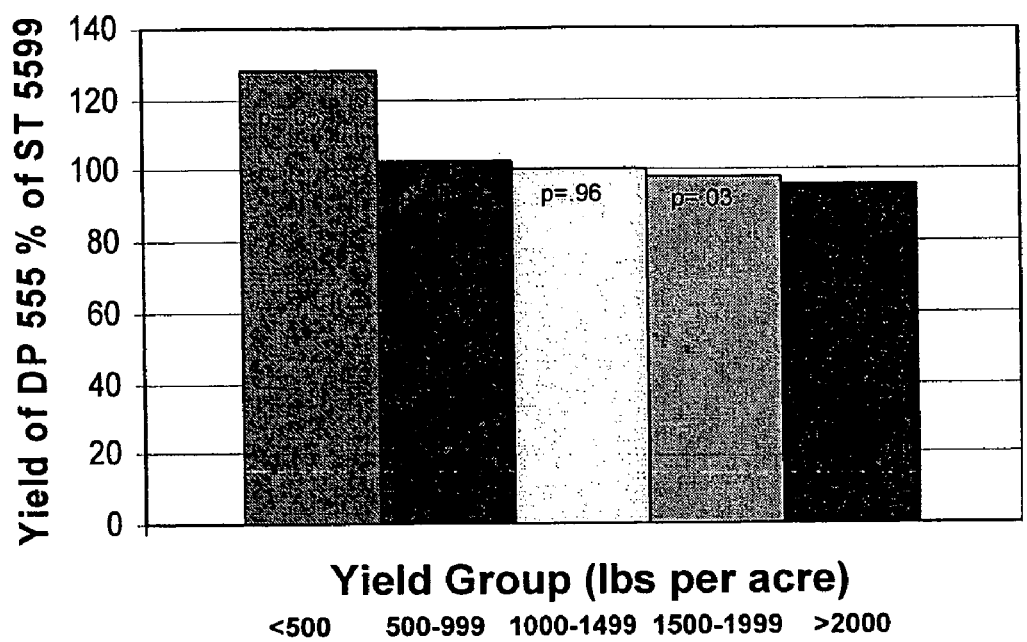
FIG. 16 provides fiber yield ratio for a low oil cotton variety (DP 555 BG/RR) and a high oil cotton variety (ST 5599 BG/RR).

Drought Stress Tolerance of Two Cotton Varieties with Varying Levels of Seed Oil Content Beyond the fertilizer and soil nutrition benefits derived from reducing N, P and K in the seed, an additional benefit derives from the metabolic savings to the plant as the biosynthesis of protein and phytate requires substantial amounts of reduced carbon precursers and high energy reductants. Minimizing the need for these two inputs allows greater plant metabolic resources that can be used to generate new leaves, roots and maintain plant defenses against diseases and nematodes. To establish differences in seed oil content a low oil variety (DP 555 BG/RR, oil content of 14.0%) and a high oil variety (ST 5599BR, oil content of 18.2%) were compared at 4 midsouth locations with 4 replications. The LSD 0.05 was 1.15% oil. To establish the yield performance under a wide range of environments, these same two varieties were compared at 971 U.S. locations which where sorted into 5 location groups based on the yield of ST 5599RR. FIG. 16 shows the mean yield of the low oil and high oil varieties for each group. The interaction of variety by group was highly significant, p=0.008. The low oil variety substantially outperformed the high oil variety only in the low yield group, while they were comparable in higher yield groups. This provides support for the proposed mechanism that varieties with reduced seed storage have greater metabolic resources for new root and leaf development that can contribute to yield stability under low yielding (stress) environments.

Example 11

Cartoon of Preferred Embodiment

Figure 17:
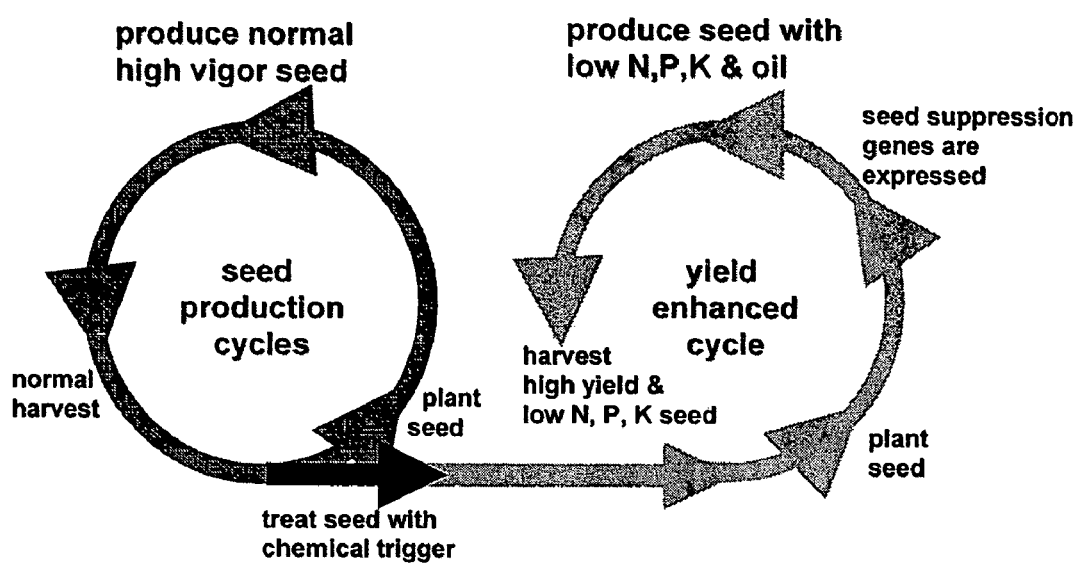
FIG. 17 is a cartoon of the seed production generation and fiber production generation cycles of plants made according to the methods disclosed herein.

FIG. 17. details a cartoon diagram for the preferred embodiment using a gene switch mediated dominant negative mutant Canola FAD2. The seed production cycle allows selfing and seed increase. Seed from any of these seed production cycles can be used in the yield enhancing cycle by treating the seed with the appropriate chemical trigger thereby turning on the gene switch controlled FAD2 during the subsequent yield enhancing cycle. During the yield enhancing cycle, abundant fiber production is achieved in fields with lower levels of soil fertility as the resulting cotton seeds have lower content of oil, N, P and K.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method of producing a high-fiber-yield cotton plant, comprising the steps of:
   (a) inserting into a cell of a cotton plant a transgene to give a modified cotton cell, wherein, the transgene comprises a sequence under the control of an inducible promoter, and the sequence encodes a protein, wherein the expression of the protein reduces the activity of one or more enzymes that function in oil production in cottonseed; and
   (b) regenerating a whole cotton plant from the modified cotton plant cell to give a modified cotton plant;
   (c) selecting the high-fiber-yield cotton plant containing the transgene from one or more modified cotton plants;
   (d) applying an inducing agent to activate the inducible promoter in the high-fiber-yield cotton plant;
   wherein the sequence is a mutant delta-12 fatty acid desaturase (FAD2) gene from canola; and
   wherein the high-fiber-yield cotton plant has increased fiber yield relative to a control cotton plant, when the transgene in the high-fiber-yield cotton plant is expressed due to the activation by the inducible promoter.

2. A method of producing a high-fiber-yield cotton plant, comprising the steps of:
   (a) inserting into a cell of a cotton plant a transgene to give a modified cotton plant cell, wherein the transgene comprises a sequence encoding a mutant canola delta-12 fatty acid desaturase (FAD2) under control of an inducible promoter, expression of which reduces the activity of oil production in cottonseed;
   (b) regenerating a whole cotton plant from the modified cotton plant cell to give a modified cotton plant; and
   (c) selecting the high-fiber-yield cotton plant containing the transgene from one or more modified cotton plants;
   wherein the high-fiber-yield cotton plant has increased fiber yield relative to a control cotton plant, and wherein fiber yield of the high fiber-yield-cotton plant is increased when the transgene is expressed due to the activation by the inducible promoter.

3. The method of claim 2 wherein the linkage between said transgene and said inducible promoter of cotton is convertible from an inoperable to an operable linkage by the action of a gene switch.

4. A method of producing a high-fiber-yield cotton plant, comprising the steps of:
   (a) expressing in a cell of a cotton plant a transgene to give a modified cotton cell, wherein the transgene comprises a sequence encoding a mutant canola delta-12 fatty acid desaturase (FAD2), wherein said FAD2 is a dominant negative allele;
   (b) regenerating a whole cotton plant from the modified cotton plant cell; and
   (c) selecting the high-fiber-yield cotton plant containing the expressed transgene from one or more modified cotton plants;
   wherein the high-fiber-yield cotton plant has increased fiber yield relative to a control cotton plant, and wherein fiber yield of the high-fiber-yield cotton plant is increased when the transgene is expressed.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Canola Brassica

<400> SEQUENCE: 1
atgcaagtgt ctcctccctc c                    21

<210> SEQ ID NO 2
<211> LENGTH: 20

```
<212> TYPE: DNA
<213> ORGANISM: Canola Brassica

<400> SEQUENCE: 2
cgttaacatc acggtcgctc                                              20
```